US008922330B2

(12) United States Patent
Moberg et al.

(10) Patent No.: US 8,922,330 B2
(45) Date of Patent: Dec. 30, 2014

(54) COORDINATION OF CONTROL COMMANDS IN A MEDICAL DEVICE SYSTEM HAVING AT LEAST ONE THERAPY DELIVERY DEVICE AND AT LEAST ONE WIRELESS CONTROLLER DEVICE

(71) Applicant: Medtronic Minimed, Inc., Northridge, CA (US)

(72) Inventors: Sheldon B. Moberg, Thousand Oaks, CA (US); Ian B. Hanson, Wayne, PA (US)

(73) Assignee: Medtronic MiniMed, Inc., Northridge, CA (US)

( * ) Notice: Subject to any disclaimer, the term of this patent is extended or adjusted under 35 U.S.C. 154(b) by 213 days.

(21) Appl. No.: 13/690,160

(22) Filed: Nov. 30, 2012

(65) Prior Publication Data

US 2013/0090625 A1    Apr. 11, 2013

Related U.S. Application Data

(62) Division of application No. 12/500,272, filed on Jul. 9, 2009, now Pat. No. 8,344,847.

(51) Int. Cl.
*G05B 23/02* (2006.01)
*A61M 5/172* (2006.01)
*G06F 19/00* (2011.01)

(52) U.S. Cl.
CPC ........... *A61M 5/172* (2013.01); *G06F 19/3406* (2013.01); *G06F 19/3418* (2013.01); *G06F 19/3481* (2013.01); *A61M 2205/505* (2013.01)

USPC .......... 340/3.1; 340/3.2; 340/506; 340/539.1; 340/539.12

(58) Field of Classification Search
CPC ..................................... G06F 19/3406
USPC .................... 340/3.2, 3.1, 506, 359.1, 359.2; 600/118, 126, 300; 601/150
See application file for complete search history.

(56) References Cited

U.S. PATENT DOCUMENTS

| 6,127,931 A * | 10/2000 | Mohr ......................... 340/573.4 |
| 6,714,132 B2 * | 3/2004 | Edwards et al. ........... 340/573.1 |
| 6,790,198 B1 * | 9/2004 | White et al. ................. 604/151 |
| 7,986,802 B2 * | 7/2011 | Ziller ............................ 381/334 |
| 8,009,014 B2 * | 8/2011 | Eberhart et al. ............... 340/5.2 |
| 8,344,847 B2 * | 1/2013 | Moberg et al. ................ 340/3.2 |
| 2006/0197653 A1 * | 9/2006 | Kung et al. ................ 340/10.34 |

* cited by examiner

*Primary Examiner* — Nam V Nguyen
(74) *Attorney, Agent, or Firm* — Ingrassia Fisher & Lorenz, P.C.

(57) ABSTRACT

A medical device system includes at least one controllable patient-worn or patient-carried medical device, and a plurality of controller devices that are capable of independently controlling features or functions of the patient medical device. Control commands and other data is wirelessly communicated among the patient medical device and the multiple controller devices. A number of techniques, protocols, and other measures are provided to coordinate wireless communication between the various devices in a medical device system. These control command coordination processes address situations where conflicting, redundant, or concurrent control commands might be independently issued by the multiple controller devices.

11 Claims, 20 Drawing Sheets

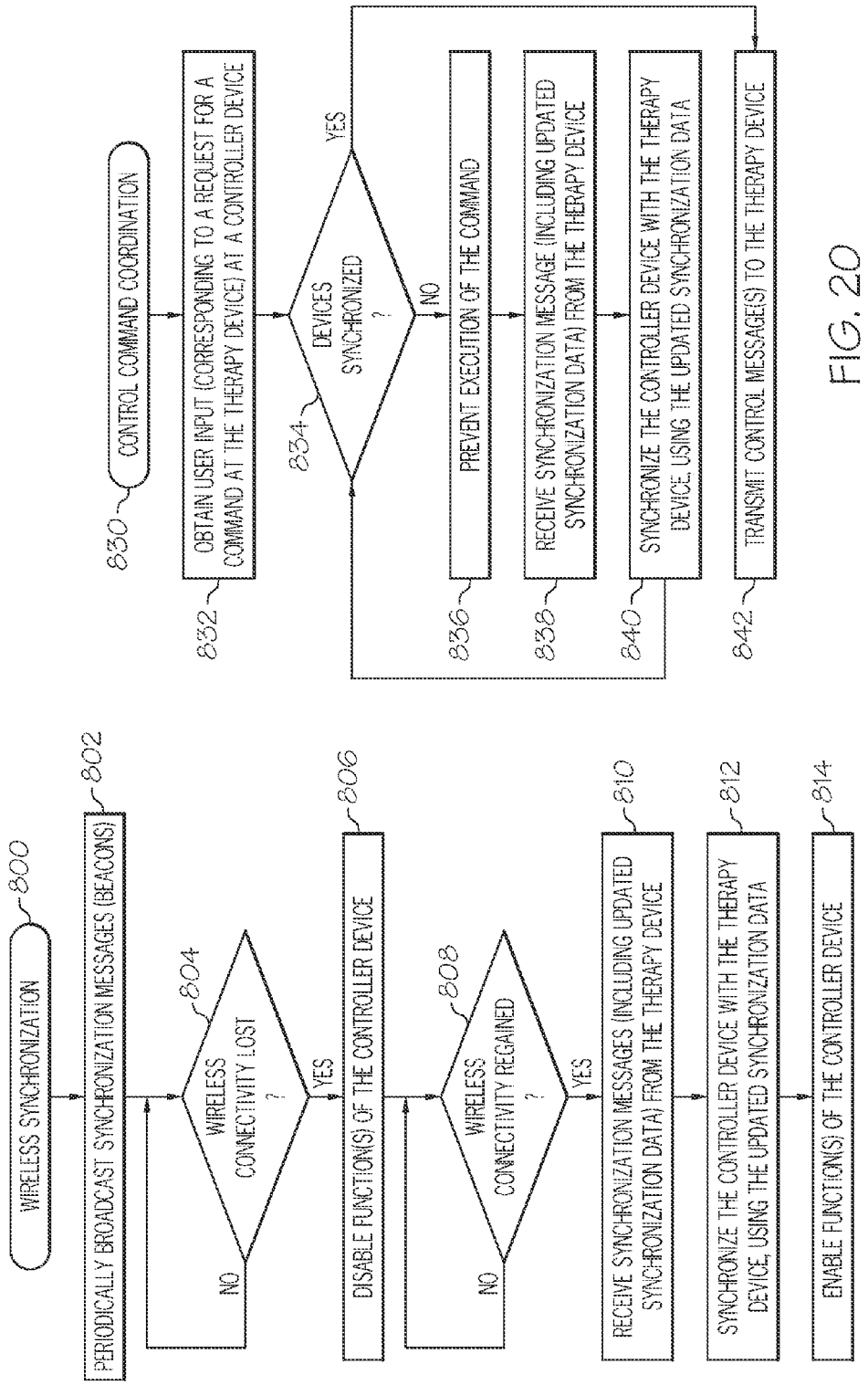

COORDINATION OF CONTROL COMMANDS IN A MEDICAL DEVICE SYSTEM HAVING AT LEAST ONE THERAPY DELIVERY DEVICE AND AT LEAST ONE WIRELESS CONTROLLER DEVICE

CROSS-REFERENCE TO RELATED APPLICATIONS

This application is a divisional of U.S. patent application Ser. No. 12/500,272 (filed on Jul. 9, 2009 and issued on Jan. 1, 2013 as U.S. Pat. No. 8,344,847). Moreover, the subject matter of this application is related to the subject matter described in U.S. patent application Ser. No. 12/500,281 (filed on Jul. 9, 2009), U.S. patent application Ser. No. 12/500,283 (filed on Jul. 9, 2009), U.S. patent application Ser. No. 12/500,295 (filed on Jul. 9, 2009), U.S. patent application Ser. No. 12/500,313 (filed on Jul. 9, 2009), and U.S. patent application Ser. No. 12/500,317 (filed on Jul. 9, 2009).

TECHNICAL FIELD

Embodiments of the disclosed subject matter relate generally to medical devices and medical device networks, such as infusion systems that deliver fluids into a patient's body. More particularly, embodiments of the subject matter relate to techniques and methods for managing control commands in a medical device system having a plurality of controller devices for one remotely controlled medical device.

BACKGROUND

Portable medical devices having wireless data communication capabilities are becoming increasingly popular, especially for patients that have conditions that must be monitored on a continuous or frequent basis. For example, diabetics are usually required to modify and monitor their daily lifestyle to keep their body in balance, in particular, their blood glucose (BG) levels. Individuals with Type 1 diabetes and some individuals with Type 2 diabetes use insulin to control their BG levels. To do so, diabetics routinely keep strict schedules, including ingesting timely nutritious meals, partaking in exercise, monitoring BG levels daily, and adjusting and administering insulin dosages accordingly. Diabetics may utilize wireless medical devices that are deployed in a network environment in a manner that facilitates data communication between two or more separate devices.

The prior art includes a number of insulin pump systems that are designed to deliver accurate and measured doses of insulin via infusion sets (an infusion set delivers the insulin through a small diameter tube that terminates at a cannula inserted under the patient's skin). In lieu of a syringe, the patient can simply activate the insulin pump to administer an insulin bolus as needed, for example, in response to the patient's current BG level. A patient can measure his BG level using a BG measurement device, such as a test strip meter, a continuous glucose measurement system, or the like. BG measurement devices use various methods to measure the BG level of a patient, such as a sample of the patient's blood, a sensor in contact with a bodily fluid, an optical sensor, an enzymatic sensor, or a fluorescent sensor. When the BG measurement device has generated a BG measurement, the measurement is displayed on the BG measurement device. A continuous glucose monitoring system can monitor the patient's BG level in real time.

Insulin pumps and other portable medical devices may also be configured to communicate with remote controller devices, monitoring or display devices, BG meters, and other devices associated with such an infusion system. It may be desirable to use multiple wireless controller devices to remotely control one medical device, such as an infusion pump. For example, a patient having a wearable or otherwise portable infusion device may have one or more controller devices at home, another controller device at the office, and yet another controller device in a vehicle. Moreover, it may be desirable to enable different people to remotely control a single infusion device. Thus, the patient may have one wireless controller, and a caregiver (such as a parent) may have another wireless controller, both having independent control capabilities. Furthermore, a patient may use two different remotely controllable medical devices, which may be wirelessly controlled by one or more wireless controllers.

The communication, processing, and execution of remote control commands is somewhat straightforward in a basic medical device system having only one medical device and only one corresponding wireless controller device. As more compatible devices are introduced, however, conflicting or redundant instructions and commands might be issued concurrently (or very close in time) by different controller devices. Conflicting or duplicative commands may be tolerable or troublesome, depending upon the functions or features associated with those commands. Consequently, it becomes increasingly important to manage, regulate, and coordinate the manner in which control commands are handled and processed in a medical device system having a plurality of controller devices for one medical device.

A personal infusion system, such as an insulin infusion system that is worn or carried by a patient, might utilize consumable, refillable, or replaceable parts, components, or items. For example, an insulin infusion pump may cooperate with replaceable or replenishable items such as a continuous glucose sensor, an infusion set, and an insulin reservoir. Such consumables can usually be obtained from a physician, from the equipment manufacturer, and/or from a pharmacy. Some existing infusion systems include reminder or alert features that notify the user whenever it is time to replace or refill a consumable item.

The prior art includes portable medical devices that utilize display elements, which can be used to display information associated with the operation of the medical devices. For example, the display element of an insulin infusion pump (or a remote controller device for the pump) can be used to display a graph, a chart, or other visual representation of data related to the patient and/or to the operation of the pump. In this regard, the pump might display a graph of the patient's glucose level versus time. Due to the small size of the display element of a portable pump device, the time period displayed at any given moment will be limited (e.g., two hours, four hours, twelve hours). If the visible time scale is changed without altering the vertical scale, the slope characteristics of the graphed data will change accordingly. Thus, a relatively high slope (whether increasing or decreasing) may have more or less significance, depending upon the chosen time scale. Consequently, the user may not fully appreciate the significance of slope trends and variations in the charted data, unless the user is always aware of the selected time scale.

Certain types of portable medical devices may implement security features to ensure that sensitive, private, or important functions are not accidentally activated, and/or to ensure that such functions can only be activated by authorized individuals. For example, an infusion pump or specific functions of the pump may be password protected to ensure that only the patient or an authorized caregiver can administer therapy with the pump. Conventional security measures can be cumbersome, difficult to program, and/or inconvenient for the user. For example, usernames and passwords rely on memorization, which introduces human error. Moreover, usernames and passwords can be compromised if the user discloses them to others or documents them in a manner that can be accessed by unauthorized persons.

BRIEF SUMMARY

A method of coordinating control commands in a medical device system is provided. The medical device system includes a medical device for a patient, and a plurality of wireless controller devices for the medical device, where each of the wireless controller devices is capable of independently issuing control commands for the medical device. The method involves wirelessly broadcasting a lockout message from a first controller device of the plurality of wireless controller devices, the lockout message being formatted to disable at least one function of a second controller device of the plurality of wireless controller devices upon receipt of the lockout message at the second controller device. Thereafter, the method wirelessly transmits a control command from the first controller device, the control command being formatted to control a function of the medical device upon receipt of the control command by the medical device. Thereafter, an unlock message is wirelessly broadcast from the first controller device, the unlock message being formatted to clear the lockout message at the second controller device upon receipt of the unlock message at the second controller device.

Another method of coordinating control commands in a medical device system is also provided. The medical device system includes a medical device for a patient, and a plurality of wireless controller devices for the medical device, each of the wireless controller devices being capable of independently issuing control commands for the medical device. This method involves wirelessly receiving a lockout message at a first controller device of the plurality of wireless controller devices, wherein the lockout message is broadcast by a second controller device of the plurality of wireless controller devices in preparation of issuing a control command for the medical device. The method continues by disabling at least one function of the first controller device upon receipt of the lockout message at the first controller device, resulting in at least one disabled function. Thereafter, an unlock message is wirelessly received at the first controller device, and the at least one disabled function is enabled upon receipt of the unlock message at the first controller device.

Also provided is a method of coordinating control commands in a medical device system having a medical device that delivers therapy to a patient, and a plurality of wireless controller devices for the medical device. This method detects user interaction with the medical device and, after detecting the user interaction, the method wirelessly broadcasts a disable message from the medical device. The disable message conveys instructions intended to at least partially disable control functions of the plurality of wireless controller devices. Thereafter, the method executes a function of the medical device and, after execution of the function, wirelessly broadcasts an enable message from the medical device. The enable message conveys instructions intended to override the effect of the disable message.

Another method of coordinating control commands in a medical device system is also provided. The medical device system includes a medical device that delivers therapy to a patient, and a plurality of wireless controller devices for the medical device. This method begins by wirelessly receiving a disable message at the plurality of wireless controller devices, wherein the disable message is broadcast from the medical device in preparation of executing a control command at the medical device. In response to receiving the disable message, the method at least partially disables control functions of the plurality of wireless controller devices, resulting in at least one disabled function. Thereafter, an enable message is wirelessly received at the plurality of wireless controller devices, and, in response to receiving the enable message, the at least one disabled function of the plurality of wireless controller devices is enabled.

Yet another method of coordinating control commands in a medical device system is provided. The medical device system includes a medical device that delivers therapy to a patient, and a wireless controller device for the medical device. This method involves obtaining a user input at the wireless controller device, the user input corresponding to a request to initiate a command that influences therapy delivered by the medical device. In response to the user input, the method checks a synchronization status between the wireless controller device and the medical device. The method continues by transmitting, to the medical device, a control message for the command only when the checking step confirms that the wireless controller device is synchronized with the medical device.

Another method of coordinating control commands in a medical device system is provided. The medical device system includes a medical device that delivers therapy to a patient, and a plurality of wireless controller devices for the medical device. This method begins by wirelessly receiving a control command that is formatted to control a function of the medical device, the control command originating from an active controller device of the plurality of wireless controller devices. In response to receiving the control command, a disable message is wirelessly broadcast from the medical device, the disable message conveying instructions intended to at least partially disable control functions of the plurality of wireless controller devices. The control command is then processed to execute the function.

Also provided is a method of operating a portable medical device having one or more consumables associated therewith. This method automatically determines, with the portable medical device, when a consumable associated with the portable medical device requires replacement. In response to the automatic determination, the method displays an active link to a vendor of the consumable. In response to selection of the active link, the method initiates an electronic transaction for the consumable, using the portable medical device.

A portable medical device is provided. The medical device includes: a tracking module configured to determine when a replenishable item associated with the portable medical device needs to be replenished; and an e-commerce module operatively coupled to the tracking module, the e-commerce module initiating an order of the replenishable item when the tracking module determines that the replenishable item needs to be replenished.

A method of operating a portable medical device that facilitates treatment of a medical condition of a patient is also provided. This method automatically determines, with the portable medical device, a need to acquire an item associated with operation of the portable medical device, and/or associated with treatment of the medical condition. The method also obtains geographic position data that indicates a location of the portable medical device, and identifies, based upon the geographic position data, a provider of the item, wherein the provider maintains inventory of the item at a facility located within a predetermined distance from the location of the portable medical device. The method also initiates, with the portable medical device, an e-commerce transaction with the provider, the e-commerce transaction including an electronic order for the item.

Another method of controlling operation of a portable medical device having one or more consumables associated therewith is provided. This method involves: receiving status data corresponding to operating status of the portable medical device; determining, based upon analysis of the status data, when a consumable associated with the portable medical device requires replacement or replenishment; in response to the determining step, generating a message that indicates a need to replace or replenish the consumable; and communicating the message to the portable medical device.

Also provided is another method of operating a portable medical device having one or more consumables associated therewith. This method begins by obtaining status data that indicates a remaining quantity, supply, or inventory of a consumable used by the portable medical device. The status data is uploaded to a remote computing device that is physically distinct and separate from the portable medical device. The method receives at least one message that indicates a need to replace or replenish the consumable. The at least one message is initiated by the remote computing device when the status data indicates that the consumable should be replaced or replenished.

A portable medical device is also provided. The medical device includes: a tracking module that obtains status data indicative of a remaining quantity, supply, or inventory of a replenishable product used by the portable medical device; a data communication module operatively coupled to the tracking module, the data communication module being configured to transfer the status data to a remote computing device, and configured to receive a message that indicates a need to replace or refill the replenishable product, the message being initiated by the remote computing device when the status data indicates that the replenishable product should be replaced or refilled; and an e-commerce module configured to initiate a transaction for the replenishable product.

Also provided is a method of controlling operation of a portable medical device that facilitates treatment of a medical condition of a patient. The method receives patient data associated with the medical condition of the patient, and determines, based upon analysis of the patient data, when the medical condition of the patient requires attention. In response to the determination, the method communicates at least one advertisement to the portable medical device, wherein the at least one advertisement is for goods and/or services related to treatment of the medical condition.

Another method of operating a portable medical device is provided. The medical device has one or more consumables associated therewith, and the method involves: automatically determining, with the portable medical device, when a consumable associated with the portable medical device requires replacement or replenishment; and in response to the automatically determining step, presenting an advertisement at the portable medical device, the advertisement identifying a supplier, seller, or vendor of the consumable.

Also provided is a method of operating a portable medical device that facilitates treatment of a medical condition of a patient. This method involves: automatically determining, with the portable medical device, when the medical condition of the patient requires attention; and in response to the automatically determining step, presenting an advertisement at the portable medical device, the advertisement identifying a supplier, seller, or provider of goods and/or services associated with treatment of the medical condition.

A portable medical device that facilitates treatment of a medical condition of a patient is provided. The portable medical device includes: a tracking module configured to determine when the medical condition of the patient requires attention; and an advertisement server module operatively coupled to the tracking module. The advertisement server module is configured to present an advertisement at the portable medical device when the tracking module determines that the medical condition requires attention, wherein the advertisement is contextually related to treatment of the medical condition.

Moreover, a method for presenting information on a display element of a portable medical device is provided. This method involves: rendering, on the display element, a first graphical representation of information associated with operation of the portable medical device; obtaining, at the portable medical device, a user-initiated display panning command; and rendering, on the display element, a second graphical representation of the information. At least a portion of the second graphical representation is not included in the first graphical representation. In addition, rendering of the second graphical representation is performed in response to the user-initiated display panning command.

Also provided is a method of providing an intuitive graphical display of patient data for a medical device having a display element. This method obtains measurement data corresponding to values of a physiological characteristic measured over a period of time, and renders a graphical representation of a portion of the measurement data on the display element, resulting in a display of the values of the physiological characteristic measured during a first interval of the period of time. Thereafter, a user-initiated display panning command is processed. In response to the user-initiated display panning command, the method dynamically pans the graphical representation while updating the portion of the measurement data. Thereafter, the method displays the values of the physiological characteristic measured during a second interval of the period of time.

A medical device is also provided. The medical device includes at least one memory element configured to store physiological characteristic data corresponding to values of a physiological characteristic for a patient. The medical device also includes a graphics engine configured to generate image rendering display commands associated with the physiological characteristic data, and a display element coupled to the graphics engine. The display element is configured to receive the image rendering display commands and, in response thereto, render visual representations of the physiological characteristic data. The medical device also includes a human-machine interface element operatively coupled to the graphics engine, and configured to generate display shifting commands in response to user interaction therewith. The display element renders a visual representation of the physiological characteristic data such that it corresponds to a first time interval. Moreover, in response to a display shifting command generated by the human-machine interface element, the display element updates the visual representation of the physiological characteristic data such that it corresponds to a second time interval.

Another embodiment of a medical device is provided. This medical device includes: a security module configured to regulate operations of the medical device; a fingerprint reader operatively coupled to the security module, the fingerprint reader configured to detect fingerprints, and to generate fingerprint data corresponding to swiped fingerprints; and at least one memory element operatively coupled to the security module, and configured to maintain a list of fingerprint-secured operations of the medical device, each of the fingerprint-secured operations being linked to a respective assigned set of identifiable fingerprint data. The security module is configured to analyze a swiped set of fingerprint data, compare the swiped set of fingerprint data to identifiable fingerprint data maintained in the list, and initiate one of the fingerprint-secured operations when the swiped set of fingerprint data satisfies matching criteria for its respective assigned set of identifiable fingerprint data.

A medical device system is also provided. The system includes a portable therapy delivery device that can be worn or carried by a patient, and a controller configured to remotely control delivery of therapy to the patient via the portable therapy delivery device. The controller includes a security module configured to regulate operations of the controller and/or the portable therapy delivery device, and a fingerprint reader operatively coupled to the security module. The fingerprint reader is configured to read fingerprints, and to generate fingerprint data corresponding to swiped fingerprints. The controller also includes at least one memory element operatively coupled to the security module, and configured to maintain a list of fingerprint-secured operations. Each of the fingerprint-secured operations is linked to a respective assigned set of identifiable fingerprint data. The security module is configured to analyze a swiped set of fingerprint data, compare the swiped set of fingerprint data to identifiable fingerprint data maintained in the list, and initiate one of the fingerprint-secured operations when the swiped set of fingerprint data satisfies matching criteria for its respective assigned set of identifiable fingerprint data.

Also provided is a method of operating a medical device in a secure manner. This method maintains a list of fingerprint-secured operations and associated fingerprint data for the medical device, where each of the fingerprint-secured operations is associated with a different fingerprint. The method obtains swiped fingerprint data, determines that the swiped fingerprint data satisfies matching criteria for the associated fingerprint data for a fingerprint-secured operation in the list, and, in response to the determining step, activates the fingerprint-secured operation.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 19 is a flow chart that illustrates an embodiment of a wireless synchronization process suitable for use with a medical device system;

FIG. 20 is a flow chart that illustrates an embodiment of a fourth embodiment of a control command coordination process suitable for use with a medical device system;

DETAILED DESCRIPTION

Figure 1:
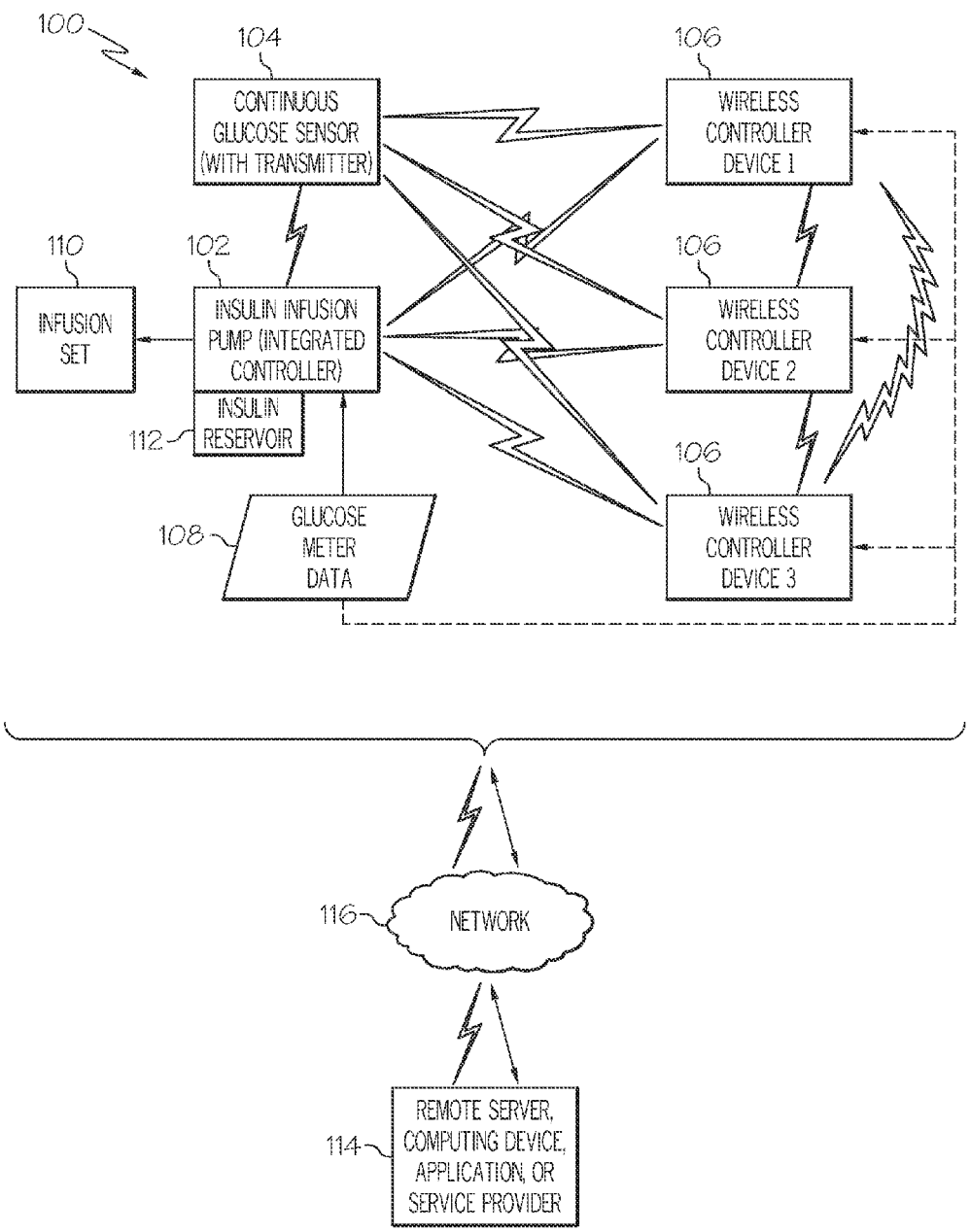
FIG. 1 is a schematic representation of an embodiment of an insulin infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Techniques and technologies may be described herein in terms of functional and/or logical block components and various processing steps. It should be appreciated that such block components may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments may be practiced in conjunction with any number of data transmission protocols and that the system described herein is merely one suitable example.

For or the sake of brevity, conventional techniques related to infusion system operation, insulin pump and/or infusion set operation, blood glucose sensing and monitoring, signal processing, data transmission, signaling, network control, and other functional aspects of the systems (and the individual operating components of the systems) may not be described in detail here. Examples of infusion pumps and/or communication options may be of the type described in, but not limited to, U.S. Pat. Nos. 4,562,751; 4,685,903; 5,080,653; 5,505,709; 5,097,122; 6,554,798; 6,558,320; 6,558,351; 6,641,533; 6,659,980; 6,752,787; 6,817,990; and 6,932,584, which are herein incorporated by reference. Examples of glucose sensing and/or monitoring devices maybe be of the type described in, but not limited to, U.S. Pat. Nos. 6,484,045; 6,809,653; 6,892,085; and 6,895,263, which are herein incorporated by reference.

The systems, methods, and technologies described below can be implemented in a medical device system having any number of different medical device types, along with any number of compatible or cooperating devices that are used with the different medical devices. The different medical devices may be associated with a single patient or with multiple patients. The medical devices may be designed to treat one or more different medical conditions, and each medical device might have a specific function in the context of an overall patient treatment or healthcare plan. The non-limiting examples described below relate to a medical device system used to treat diabetes, although embodiments of the disclosed subject matter are not so limited.

For ease of description, the examples provided below assume that one primary medical device for a single patient (e.g., a therapy delivery device or medication delivery device, such as an insulin infusion pump) can wirelessly communicate with a plurality of physically distinct controller devices. It should be appreciated that the techniques and technologies described herein can also be extended to accommodate a scenario where a single patient has two or more different medical devices, and/or to accommodate a more expansive deployment that contemplates a plurality of different patients. Moreover, the multiple controller devices may be owned or operated by the patient only, by the patient and at least one other person such as a caregiver, by one person other than the patient, or by more than one person other than the patient.

Certain preferred embodiments utilize portable devices that can be worn, carried, or held by the user. Alternatively, a given device could be designed as a somewhat stationary component (e.g., a bedside controller or monitor, a computer-based controller, or an appliance). Regardless of whether a device is mobile or stationary, it may be capable of wireless communication with other devices in the medical device system. In practice, the medical devices can form a relatively short-range wireless and localized network, which may be akin to a personal area network, a body area network, or a home network. The exemplary embodiments described below contemplate such a localized network, which is indicative of a typical deployment for a single patient.

FIG. 1 is a schematic representation of an embodiment of an insulin infusion system 100. Insulin infusion system 100 represents one possible implementation of a medical device system that is configured to deliver therapy to a patient. Insulin infusion system 100 controls the infusion of insulin into the body of a user. Briefly, insulin infusion system 100 includes a number of devices that communicate (unidirectional or bidirectional) with each other. For this simplified embodiment, insulin infusion system 100 generally includes, without limitation: an insulin infusion pump 102; at least one physiological characteristic sensor, which may be realized as a continuous glucose sensor transmitter 104; and a plurality of wireless controller devices 106. Insulin infusion system 100 may also include or cooperate with a glucose meter (not shown) that provides glucose meter data 108, an infusion set 110 for insulin infusion pump 102, and an insulin reservoir 112 (or other means for supplying insulin) for insulin infusion pump 102. Moreover, insulin infusion system 100 may include, cooperate with, or communicate with other devices and subsystem such as, without limitation: a stationary monitor device (e.g., a bedside monitor or a hospital monitor); a vehicle communication system; a wireless-enabled watch that is compatible with insulin infusion system 100; etc.

Figure 2:
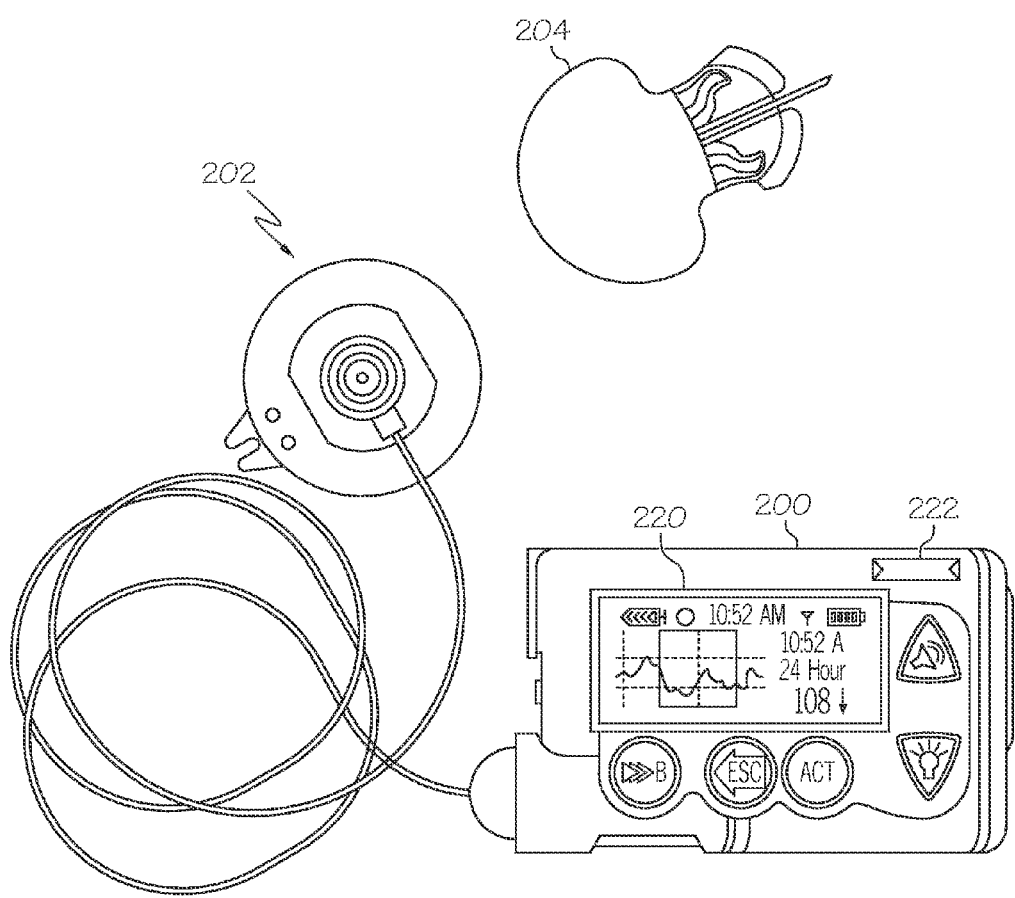
FIG. 2 is a plan view of exemplary embodiments of an infusion pump, an infusion set, and a glucose sensor/transmitter.
Figure 3:
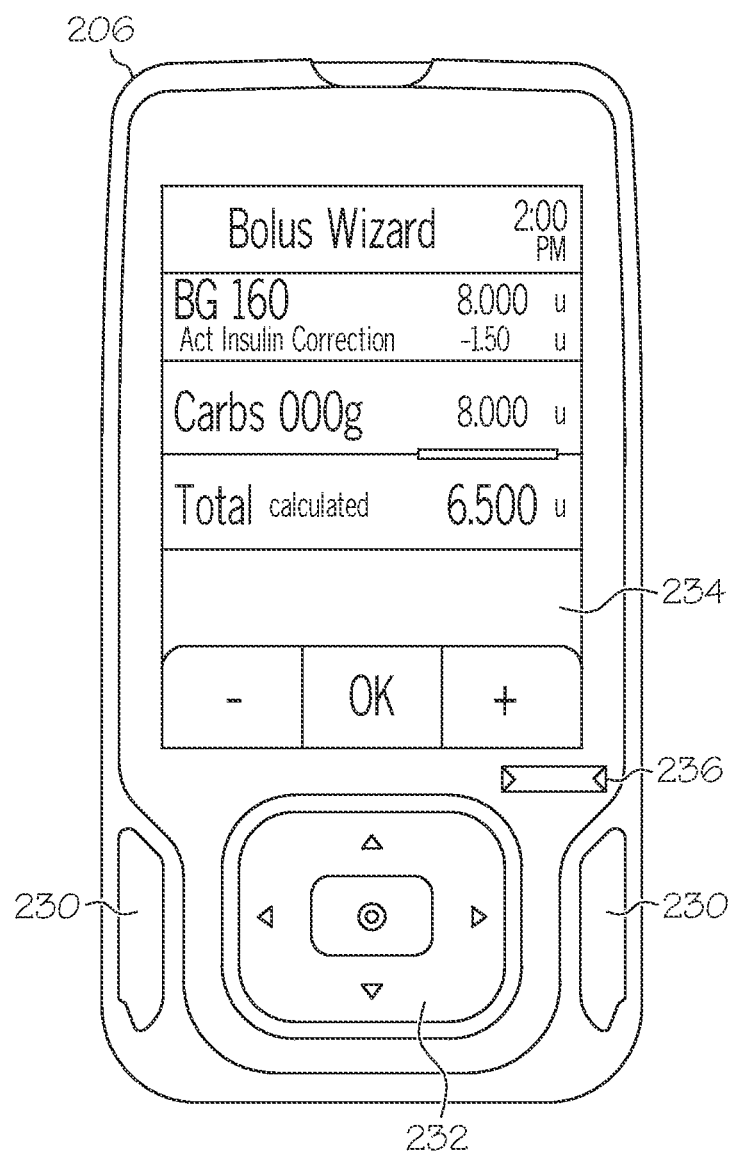
FIG. 3 is a plan view of an exemplary embodiment of a wireless controller for an infusion pump.

FIG. 2 is a plan view of exemplary embodiments of an infusion pump 200, an infusion set 202, and a glucose sensor transmitter 204, and FIG. 3 is a plan view of an exemplary embodiment of a wireless controller 206 for an infusion pump. The components shown in FIG. 2 and FIG. 3 are exemplary embodiments of insulin infusion pump 102, infusion set 110, glucose sensor transmitter 104, and wireless controller devices 106 (see FIG. 1). In practice, the components of insulin infusion system 100 can be realized using different platforms, designs, and configurations, and the embodiments shown in FIG. 2 and FIG. 3 are not exhaustive nor limiting.

In certain embodiments of insulin infusion system 100, at least one of its devices is suitably configured to communicate with a remote element 114, which may be implemented as a remote server, a server application, a remote computing device, a service provider, a network-based processor, or the like. As used here, remote element 114 is "external" to insulin infusion system 100 because it need not utilize the local data communication protocols and techniques employed within insulin infusion system 100, and because it need not be in close physical proximity to the local devices normally associated with insulin infusion system 100. The manner in which a device within insulin infusion system 100 communicates with remote element 114 may vary depending upon the particular configuration of insulin infusion system 100, the specific characteristics of the communicating devices, and the characteristics of remote element 114. For example, network communications may be routed using one or more data communication networks 116 (including a wide area network such as the internet), which may employ wireless and/or wired data transport links, as schematically depicted in FIG. 1.

For the illustrated embodiment, glucose sensor transmitter 104 wirelessly communicates with insulin infusion pump 102 and with each wireless controller device 106. In addition, insulin infusion pump 102 can wirelessly communicate with each wireless controller device 106. Similarly, wireless controller devices 106 could wirelessly communicate with each other if necessary. FIG. 1 depicts these wireless communication links as lightning bolts between the various components. Alternatively (or additionally), tangible data communication links could be utilized to transfer data between two components in insulin infusion system 100. In preferred embodiments, insulin infusion pump 102 can be remotely controlled in a wireless manner using any of the wireless controller devices 106. Notably, insulin infusion pump 102 may incorporate the functionality of a wireless controller device 106 in a native manner. In other words, insulin infusion pump 102 may be suitably configured to control itself via its native user interface. Accordingly, the following description of features, functions, and operations associated with wireless controller devices 106 may also apply (when contextually relevant) to insulin infusion pump 102.

Data communicated to (and processed by) a wireless controller device 106 may include or represent, without limitation: physiologic patient data; device status information; time and date information; alarm/alert status; GPS data corresponding to the geographic position of the user; GPS data corresponding to the geographic position of pharmacies, hospitals, restaurants, service providers, stores, etc.; and other information related to the operation, status, or condition of the patient, related to any of the devices within insulin infusion system 100, or related to insulin infusion system 100 itself. For example, such data may include or represent bolus information, basal information, or sensor information. Such data may also include or represent information entered by the patient, a caregiver, or another person having access to a device of insulin infusion system 100 or remote element 114, such as, without limitation: reminders; event markers (for meals, exercise, or the like); alarms; notifications; or the like.

Insulin infusion pump 102 is configured to deliver insulin into the body of the patient via, for example, infusion set 110. In this regard, insulin infusion pump 102 may cooperate with insulin reservoir 112, which can be a replaceable or refillable fluid reservoir for the insulin. Thus, the amount of fluid in insulin reservoir 112 (and insulin reservoir 112 itself) may be considered to be a consumable quantity, element, or product of insulin infusion system 100. Likewise, infusion set 110 can be considered to be a consumable element or component of insulin infusion system 100 because it is typically designed as a disposable unit having a limited lifespan. Similarly, glucose sensor transmitter 104 may be treated as a consumable of insulin infusion system 100. Other features, items, products, accessories, and elements of insulin infusion system 100 could also be designated as consumables.

Glucose sensor transmitter 104 is suitably configured to measure a physiologic characteristic of the patient, namely, a glucose level of the patient. In the exemplary system described here, glucose sensor transmitter 104 measures the glucose level of the patient in real time. Glucose sensor transmitter 104 includes a wireless transmitter that facilitates transmission of physiological data of the user to other devices within insulin infusion system 100, such as insulin infusion pump 102. In turn, insulin infusion pump 102 can respond to the glucose measurements obtained from glucose sensor transmitter 104 by delivering insulin as needed.

For the illustrated embodiment, infusion pump 102 and/or wireless controller devices 106 can process received sensor data in an appropriate manner. For example, a device might display the current glucose level derived from the received sensor data and/or generate an alert or otherwise indicate low or high glucose levels. As another example, a device may process the received sensor data for purposes of calibration. As yet another example, infusion pump 102 may be configured to activate its infusion mechanism in response to the received sensor data.

Any of the devices within insulin infusion system 100 may include a display and related processing logic that facilitates the display of physiologic patient data, device status information, time and date information, alarm/alert status, and other information related to the operation, status, or condition of the patient, related to any of the devices within insulin infusion system 100, or related to insulin infusion system 100 itself.

Insulin infusion pump 102 may be configured to obtain glucose meter data 108 from an appropriate source, such as a blood glucose meter or test instrument (not shown) that measures the glucose level of a user by analyzing a blood sample. The blood glucose meter may be configured to transmit the measured glucose level to infusion pump 102 and/or to any of the wireless controller devices 106. Alternatively or additionally, infusion pump 102 may include a user interface that allows the patient or caregiver to enter the measured glucose level into infusion pump 102 (a wireless controller device 106 could be similarly configured to accept user-entered glucose values).

Each wireless controller device 106 facilitates remote programming, configuration, and activation of therapy-delivering operations carried out by insulin infusion pump 102. In addition, a wireless controller device 106 could serve as a remote monitor of infusion pump 102 (and possibly other devices within insulin infusion system 100). A number of features, functions, and technologies associated with wireless controller devices 106 are described in detail below.

Referring again to FIG. 2, insulin infusion pump 200 is designed to be carried or worn by the patient (alternatively, insulin infusion pump 200 could be realized as an implantable device). This particular embodiment includes a human-machine interface (HMI) that includes several buttons that can be activated by the user. These buttons can be used to administer a bolus of insulin, to change therapy settings, to change user preferences, to select display features, and the like. In some embodiments, insulin infusion pump 200 includes a suitably configured fingerprint reader 222, scanner, swiper, or detector. Fingerprint reader 222 can be utilized to access certain fingerprint-linked operations of insulin infusion pump 200 (described in more detail below). Notably, a streamlined and remotely-controlled infusion pump need not include any HMI features, or it may include a very limited number of HMI elements. Although not required, the illustrated embodiment of insulin infusion pump 200 includes a display element 220. Display element 220 can be used to present various types of information or data to the user, such as, without limitation: the current glucose level of the patient; the time; a graph or chart of the patient's glucose level versus time; device status indicators; etc. In some embodiments, display element 220 is realized as a touch screen display element, and the functionality of fingerprint reader 222 is incorporated into the touch screen display element.

Referring now to FIG. 3, wireless controller 206 is designed as a portable device that can be carried or worn by a user. This particular embodiment includes a human-machine interface (HMI) that includes buttons 230 and a directional pad 232 that can be manipulated by the user. This embodiment also employs a touch screen display element 234 that is responsive to touching and/or physical proximity of an object. Touch screen display element 234 can be used to present various types of information or data to the user, such as, without limitation: the current glucose level of the patient; the time; a graph or chart of the patient's glucose level versus time; device status indicators; etc.

The buttons 230, directional pad 232, and touch screen display element 234 can be used to administer a bolus of insulin, to change therapy settings, to change user preferences, to select display features, and the like. Depending upon the configuration settings, options, and/or user preferences, the wireless controller 206 can be manipulated using the buttons 230 only, the touch screen display element 234 only, or both. In some embodiments, the touch screen display element 234 could be switched on and off if the feature is not desired. In some embodiments, wireless controller 206 includes a suitably configured fingerprint reader 236, scanner, swiper, or detector. Fingerprint reader 236 can be utilized to access certain fingerprint-linked operations of wireless controller 206 and/or certain fingerprint-linked operations of an insulin infusion pump under the control of wireless controller 206 (as described in more detail below). In some embodiments, the functionality of fingerprint reader 236 is incorporated into touch screen display element 234.

Figure 4:
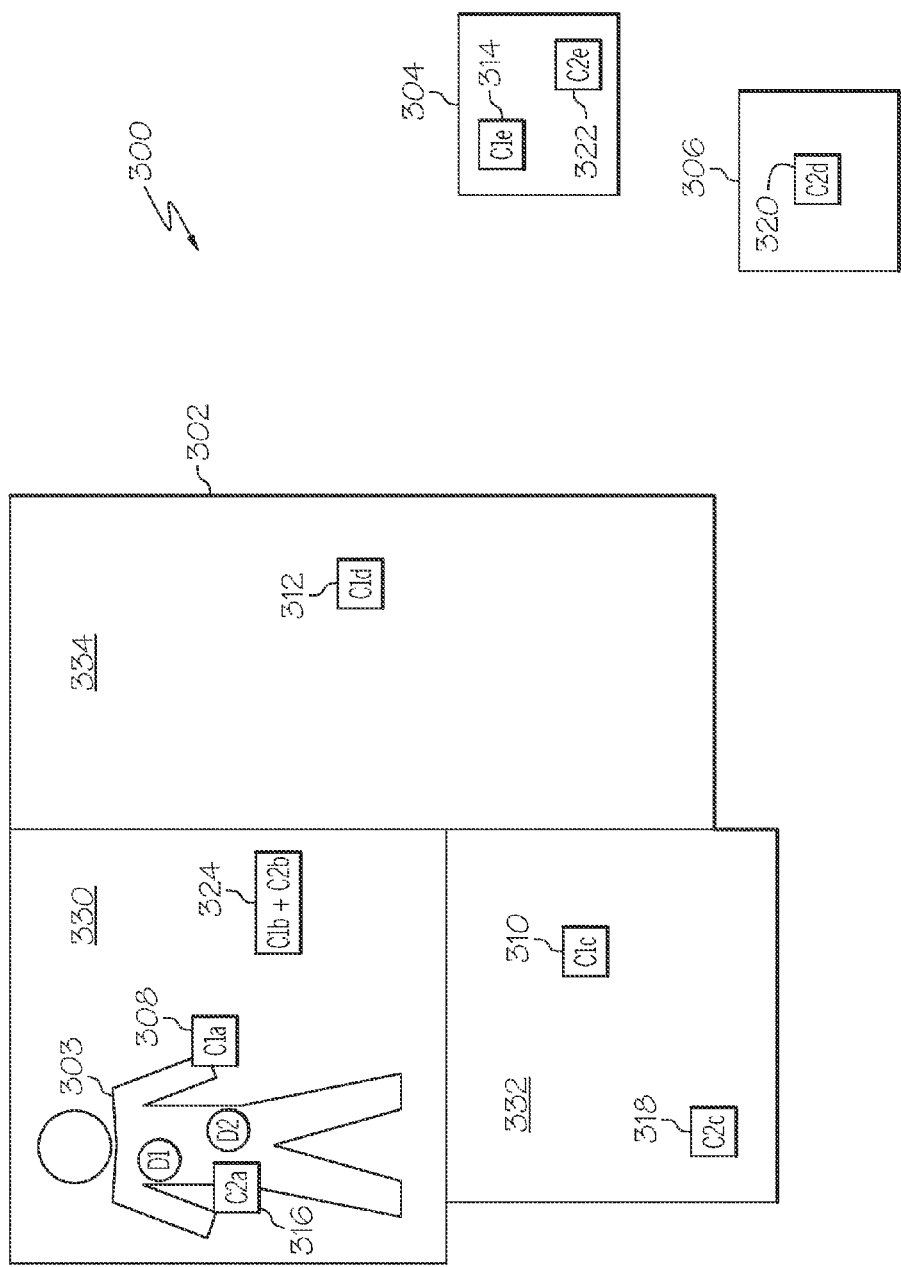
FIG. 4 is a diagram of a medical device system having multiple patient devices and multiple wireless controllers for the patient devices.

FIG. 4 is a diagram of a medical device system 300 having multiple patient devices and multiple wireless controllers for the patient devices. As mentioned previously, a medical device system for a single patient might include different therapy delivery devices and respective wireless controller devices, where a controller device is configured to control delivery of therapy to a patient via its associated therapy delivery device. Moreover, any one of the therapy delivery devices may have a plurality of associated wireless controller devices, which need not be located in the same immediate vicinity. FIG. 4 is intended to generally illustrate one possible medical device system 300 having two different therapy delivery devices (labeled D1 and D2) and a variety of wireless controller devices that are located in a physically distributed manner. FIG. 4 schematically depicts a dwelling 302, which may be any physical structure that can be occupied by a patient 303. This includes but is not limited to free-standing structures, multiple unit structures (e.g., duplex, condominium, townhouse, apartments), hotels or motels, boats, airplanes, spaceships, space stations, automobiles, remote interstellar plant habitats, vehicles, etc. FIG. 4 also schematically illustrates a first location 304 or facility that is physically distinct from dwelling 302, and a second location 306 or facility that is physically distinct from dwelling 302. For this particular example, it is assumed that first location 304 and second location 306 are beyond the normal wireless range of any wireless device located within dwelling 302.

The two therapy delivery devices D1/D2 are preferably patient-worn or patient-carried devices that remain with the patient 303 whenever they might be needed for medical treatment. Medical device system 300 includes a number of wireless controller devices that control functions of therapy delivery device D1: a first controller 308; a second controller 310; a third controller 312; and a fourth controller 314. Medical device system 300 includes a number of wireless controller devices that control functions of therapy delivery device D2: a fifth controller 316; a sixth controller 318; a seventh controller 320; and an eighth controller 322. Medical device system 300 also includes a combined controller 324, which is capable of controlling functions of both therapy delivery devices D1/D2.

FIG. 4 depicts patient 303, therapy delivery devices D1/D2, first controller 308, fifth controller 316, and combined controller 324 in a first room 330 of dwelling 302. Second controller 310 and sixth controller 318 are located in a second room 332 of dwelling 302, and third controller 312 is located in a third room 334 of dwelling 302. Under most practical conditions, all of the devices within dwelling 302 will be within wireless communication range of each other. Preferably, at least all of the devices within first room 330 are within wireless communication range of each other at all times.

First location 304 may be, for example, the place of work for patient 303, and second location 306 may be, for example, a vehicle used by patient 303. It might be convenient to have wireless controller devices that can be used when patient 303 enters first location 304 and second location 306. For instance, fourth controller 314 and eighth controller 322 could remain at first location 304 regardless of where patient 303 roams, and seventh controller 320 might remain at second location 306 regardless of where patient 303 travels. Similarly, even though some or all of the controllers located at dwelling 302 are portable, it may be desirable to keep them within the confines of dwelling 302 to ensure that at least one is always within close proximity to patient 303.

The deployment of multiple wireless controller devices for one medical device presents several challenges related to data synchronization, timing and execution of redundant or concurrent control commands, and conflicting wireless messages among the devices. A number of techniques, approaches, and methodologies that address these and other challenges are described in more detail below.

A medical device system as described here can implement a number of features, functions, operations, components, and technologies that enhance the user experience, provide security, facilitate better wireless communication among the devices, and enable e-commerce. Some of these enhancements are associated with the operation and functionality of a therapy delivery device, while others are associated with the operation and functionality of a wireless controller device. In addition, some of these enhancements involve the cooperation between one or more therapy delivery devices and/or one or more wireless controller devices. Moreover, some of the enhancements may involve one or more remote elements, such as a network-based server application.

Figure 5:
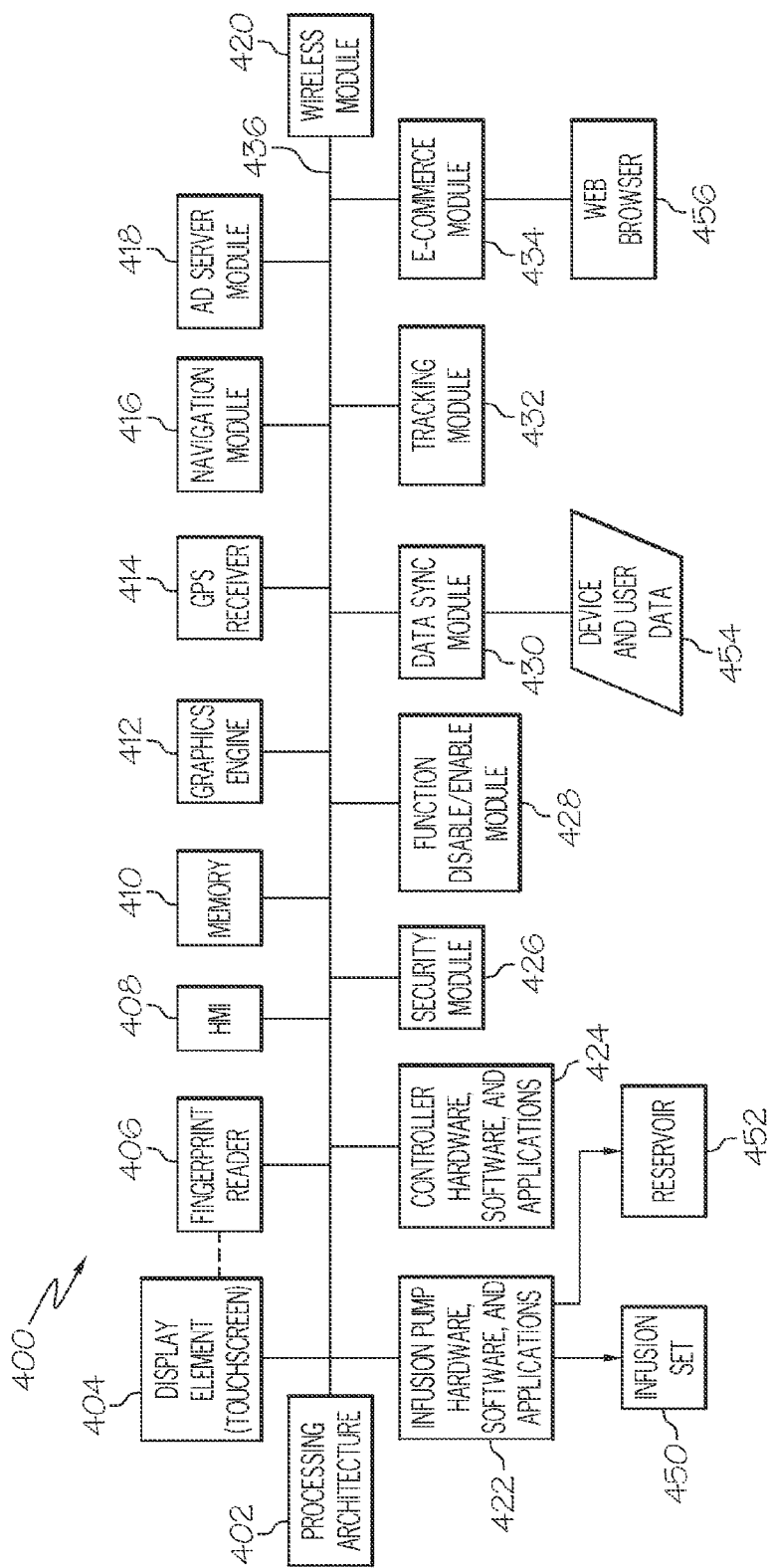
FIG. 5 is a schematic representation of a portable medical device, which may be realized as an infusion pump or a controller device.

As mentioned previously, a wireless-enabled therapy delivery device could be designed with native controller functionality. In other words, some or all of the features, functionality, components, and elements found in a wireless controller device may be incorporated into a therapy delivery device. In this regard, FIG. 5 is a schematic representation of a portable medical device 400, which may be realized as an infusion pump, a therapy delivery device, or a controller device suitable for use in a medical device system. The illustrated embodiment of medical device 400 represents a "full-featured" version; a practical embodiment need not include all of the features, modules, components, and elements depicted in FIG. 5.

This particular embodiment of medical device 400 generally includes, without limitation: a processing architecture 402, processor, or processor arrangement; a display element 404; a fingerprint reader 406; at least one human-machine interface (HMI) element 408; a suitable amount of memory 410; a graphics engine 412; a global positioning system (GPS) receiver 414; a navigation module 416; an advertisement server module 418; a wireless module 420; infusion pump hardware, software, and applications 422 (included if medical device 400 represents an infusion pump, and omitted if medical device 400 represents a controller device); controller hardware, software, and applications 424 (included if medical device 400 represents a controller device, and omitted if medical device 400 represents an infusion pump that lacks native controller functionality); a security module 426; a function disable/enable module 428; a data sync module 430; a tracking module 432; and an e-commerce module 434. The elements of medical device 400 may be coupled together via a bus 436 or any suitable interconnection architecture or arrangement that facilitates transfer of data, commands, power, etc.

Those of skill in the art will understand that the various illustrative blocks, modules, circuits, and processing logic described in connection with medical device 400 (and other devices, elements, and components disclosed here) may be implemented in hardware, computer software, firmware, a state machine, or any combination of these. To clearly illustrate this interchangeability and compatibility of hardware, firmware, and software, various illustrative components, blocks, modules, circuits, and processing steps may be described generally in terms of their functionality. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting.

Processing architecture 402 may be implemented or performed with a general purpose processor, a content addressable memory, a digital signal processor, an application specific integrated circuit, a field programmable gate array, any suitable programmable logic device, discrete gate or transistor logic, discrete hardware components, or any combination designed to perform the functions described here. A processor device may be realized as a microprocessor, a controller, a microcontroller, or a state machine. Moreover, a processor device may be implemented as a combination of computing devices, e.g., a combination of a digital signal processor and a microprocessor, a plurality of microprocessors, one or more microprocessors in conjunction with a digital signal processor core, or any other such configuration.

Processing architecture 402 may include one processor device or a plurality of cooperating processor devices. Moreover, a functional or logical module/component of medical device 400 might actually be realized or implemented with processing architecture 402. For example, graphics engine 412, navigation module 416, advertisement server module 418, security module 426, function disable/enable module 428, data sync module 430, tracking module 432 and/or e-commerce module 434 may be implemented in, or be executed by, processing architecture 402.

Display element 404 represents the primary graphical interface of medical device 400. Display element 404 may leverage known CRT, plasma, LCD, TFT, and/or other display technologies. The actual size, resolution, and operating specifications of display element 404 can be selected to suit the needs of the particular application. Notably, display element 404 may include or be realized as a touch screen display element that can accommodate touch screen techniques and technologies. In this regard, a touch screen display element can be utilized to support panning and/or scrolling features (described below) of medical device 400. In practice, display element 404 may be influenced by graphics engine 412, and driven by a suitable display driver, to enable medical device 400 to display physiological patient data, status information for infusion pumps, status information for continuous glucose sensor transmitters, clock information, alarms, alerts, and/or other information and data received or processed by medical device 400. In this regard, display element 404 could be configured to receive image rendering display commands from graphics engine 412 and, in response thereto, render visual representations of physiological characteristic data (e.g., glucose levels), render menu screens, and render other graphical representations and visual displays as needed during the operation of medical device 400.

Fingerprint reader 406 is operatively coupled to security module 426 to accommodate the processing of fingerprint-secured operations of medical device 400 and/or fingerprint-secured operations of another device that is remotely controlled by medical device 400. Fingerprint reader 406 is designed to swipe fingerprints and, in response to such swiping, generate fingerprint data that corresponds to the swiped fingerprints. In preferred embodiments, fingerprint reader 406 is a distinct functional element of medical device 400 (see FIG. 2 and FIG. 3). For such preferred embodiments, fingerprint reader 406 could be implemented as a relatively thin sensor that responds to a "swiping" touch gesture to read the fingerprint characteristics. The design, configuration, and operation of such sensors are known, and these fingerprint sensors are commonly deployed in applications such as laptop computers. In other embodiments, fingerprint reader 406 is incorporated into a touch screen display element (the dashed line in FIG. 5 indicates that fingerprint reader 406 may optionally be implemented with display element 404). In other embodiments, fingerprint reader 406 could be a standalone component or device that communicates the swiped fingerprint data to medical device 400. The relevance of fingerprint reader 406 and security module 426 is discussed further below with reference to FIG. 6 and FIG. 7.

HMI elements 408 represents the user interface features of medical device 400. Thus, HMI elements 408 may include a variety of items such as, without limitation: a keypad, keys, buttons, a keyboard, switches, knobs (which may be rotary or push/rotary), a touchpad, a microphone suitably adapted to receive voice commands, a joystick, a pointing device, an alphanumeric character entry device or touch element, a trackball, a motion sensor, a lever, a slider bar, a virtual writing tablet, or any device, component, or function that enables the user to select options, input information, or otherwise control the operation of medical device 400. In this context, HMI elements 408 may include a touch screen display element and/or fingerprint reader 406. Medical device 400 can detect manipulation of, or interaction with, HMI elements 408 and react in an appropriate manner. For example, a user could interact with HMI elements 408 to control the delivery of therapy (e.g., insulin infusion) to a patient via a therapy delivery device under the control of medical device 400. As another example, one or more of the HMI elements 408 could be operatively coupled to graphics engine 412 such that user interaction with those HMI elements 408 results in the generation of display shifting, panning, or scrolling commands that influence the manner in which information is displayed on display element 404. Display panning features are discussed in more detail below with reference to FIGS. 8-12.

Memory 410 may be realized as RAM memory, flash memory, EPROM memory, EEPROM memory, registers, a hard disk, a removable disk, a CD-ROM, or any other form of storage medium known in the art. In this regard, memory 410 can be coupled to processing architecture 402 such that processing architecture 402 can read information from, and write information to, memory 410. In the alternative, memory 410 may be integral to processing architecture 402. As an example, processing architecture 402 and memory 410 may reside in an ASIC. A functional or logical module/component of medical device 400 might be realized using program code that is maintained in memory 410. For example, graphics engine 412, navigation module 416, advertisement server module 418, security module 426, function disable/enable module 428, data sync module 430, tracking module 432 and/or e-commerce module 434 may have associated software program components that are stored in memory 410. Moreover, memory 410 can be used to store data utilized to support the operation of medical device 400, as will become apparent from the following description.

A number of display features and characteristics are described in more detail below. Accordingly, graphics engine 412 may be suitably configured to perform image, graphics, and/or video processing as needed to support the operation of medical device 400. Graphics engine 412 cooperates with the display driver (not shown) of medical device 400 to control and manage the rendering of graphical information on display element 404. For example, graphics engine 412 generates image rendering display commands associated with items to be displayed (such as physiological characteristic data, menu screens, web pages, touch screen interface features, or the like), and display element 404 receives the image rendering display commands and, in response thereto, renders corresponding graphics as needed.

GPS receiver 414 may be any commercial civilian grade receiver. In accordance with known methodologies and techniques, GPS receiver 414 obtains geographic position data (also referred to as GPS data) corresponding to the geographic position of medical device 400. The GPS data may indicate a location of medical device 400 in terms of longitude and latitude measurements. GPS receiver 414 may also provide medical device 400 with the current date, the current time, the current time zone, and other pertinent information. The geographic position data obtained from GPS receiver 414 can be used to provide a variety of location-dependent information to the user of medical device 400. The relevance of such geographic position data is discussed in more detail below with reference to FIGS. 21-24.

Navigation module 416 is suitably configured to generate and present navigation instructions, location data, and map information to the user of medical device 400. In this regard, navigation module 416 can be operatively coupled to GPS receiver 414 such that geographic position data obtained by GPS receiver 414 can be processed by navigation module 416. Navigation module 416 may leverage existing navigation and mapping technologies, and utilize preloaded or dynamically downloaded map data to provide directions to a specified location (where the directions are influenced by the geographic position of medical device). Travel guidance is typically performed using a two-step process: (1) calculate a proposed route from the current position of medical device 400 to the desired destination; and (2) present guidance instructions to the user. The guidance instructions can be updated dynamically as the user traverses the proposed route. The relevance of navigation module 416 is discussed in more detail below with reference to FIGS. 21-24.

Advertisement server module 418 can generate, access, or present advertisements at medical device 400 at certain times during operation of medical device 400. Although the advertisements could be related to anything, preferred embodiments present contextually relevant advertisements to the user of medical device 400. In this regard, the advertisements can be related to or otherwise associated with: the use of medical device 400; consumables used by or with medical device 400; the treatment of the patient's medical condition; goods and/or services that might be related to the treatment of the medical condition; goods and/or services that might be of interest to the particular user of medical device 400; etc. As described in more detail below with reference to FIGS. 21-24, advertisement server module 418 may be operatively coupled to tracking module 432; this enables advertisement server module 418 to respond when a consumable of medical device 400 needs to be replaced, replenished, refilled, or the like. Likewise, advertisement server module 418 can be suitably configured to respond when tracking module 432 determines that the medical condition requires attention or treatment.

Advertisement server module 418 can access, retrieve, or otherwise obtain advertisements that are stored and maintained locally at medical device 400. In such embodiments, contextually relevant advertisements (and possibly other types of advertisements) can be preloaded into medical device 400 and/or downloaded to medical device 400 at an appropriate time. Alternatively (or additionally), advertisement server module 418 can access, retrieve, or otherwise obtain advertisements that are stored and maintained remotely. In such embodiments, advertisement server module 418 could dynamically download advertisements on an as-needed basis, or a remote network-based application could push advertisements to advertisement server module 418 when appropriate or desirable to do so.

Advertisement server module 418 may also include or be associated with processing logic that can select, filter, or otherwise determine which advertisements to present at any given time. Filtering of advertisements could be performed in accordance with settings (e.g., user preferences) of medical device 400. In this regard, advertisement server module 418 may be operatively coupled to GPS receiver 414 such that geographic position data obtained by GPS receiver 414 can be processed by advertisement server module 418. Advertisement server module 418 can then select advertisements for goods and/or services that are available at facilities located near to the current location of medical device 400. For example, advertisement server module 418 might filter advertisements and only identify facilities, offices, or stores that are located within a predetermined distance from the current location of medical device 400 (e.g., one mile, five miles, or ten miles). Alternatively (or additionally), advertisement server module 418 might filter advertisements and only identify facilities, offices, or stores that can be reached within a predetermined travel time (e.g., a ten minute drive, a twenty minute walk, or a fifteen minute bike ride).

Wireless module 420 is a data communication module for medical device 400. Wireless module 420 is configured to support one or more wireless data communication protocols. Any number of suitable wireless data communication protocols, techniques, or methodologies may be supported by wireless module 420, including, without limitation: RF; an infrared transmission scheme such as IrDA; a short-range wireless transmission scheme such as Bluetooth; ZigBee (and other variants of the IEEE 802.15 protocol); a wireless local area network scheme such as IEEE 802.11 (any variation); IEEE 802.16 (WiMAX or any other variation); Direct Sequence Spread Spectrum; Frequency Hopping Spread Spectrum; a cellular/wireless/cordless telecommunication scheme; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. In an embodiment of medical device 400, wireless module 420 may include or be realized as hardware, software, and/or firmware, such as an RF front end, a suitably configured radio module (which may be a stand alone module or integrated with other or all functions of the device), a wireless transmitter, a wireless receiver, a wireless transceiver, an infrared sensor, an electromagnetic transducer, or the like. Moreover, wireless device 400 may include one or more antenna arrangements (which may be located inside the housing of medical device 400) that cooperate with wireless module 420.

Medical device 400 may also support data communication over a cable, a wired connection, or other physical link, using one or more wired/cabled data communication protocols. Any number of suitable data communication protocols, techniques, or methodologies may be supported by medical device 400, including, without limitation: Ethernet; home network communication protocols; USB; IEEE 1394 (Firewire); hospital network communication protocols; and proprietary data communication protocols. Although not depicted in FIG. 5, medical device 400 may support wired data communication using hardware, software, and/or firmware, such as a suitably configured and formatted port, connector, jack, plug, receptacle, socket, adaptor, or the like.

Infusion pump hardware, software, and applications 422 are utilized to carry out features, operations, and functionality that might be specific to an insulin pump implementation. Again, infusion pump hardware, software, and applications 422 need not be deployed if medical device 400 is realized as a controller device having no infusion pump. Notably, infusion pump hardware, software, and applications 422 may include or cooperate with an infusion set 450 and/or a fluid reservoir 452 (as described above with reference to FIG. 1 and FIG. 2). Infusion pump hardware, software, and applications 422 may leverage known techniques to carry out conventional infusion pump functions and operations, and such known aspects will not be described in detail here.

Controller hardware, software, and applications 424 are utilized to carry out features, operations, and functionality that might be specific to a medical device controller implementation. Again, controller hardware, software, and applications 424 need not be deployed if medical device 400 is realized as a medical device having no native control capabilities. Controller hardware, software, and applications 424 may leverage known techniques to carry out conventional controller and/or monitor device functions and operations, and such known aspects will not be described in detail here.

Security module 426 may be suitably designed to secure certain operations of medical device 400 and/or a device that is remotely controlled by medical device 400, protect medical device 400 from electronic attacks and viruses, perform authentication routines, and otherwise provide security features for medical device 400. Security features are particularly desirable with embodiments that have wireless connectivity, network access, e-commerce capabilities, and the like. In certain embodiments, security module 426 is utilized to regulate operations of medical device 400 using swiped fingerprint data. In this regard, security module 426 may be operatively coupled to fingerprint reader 406 and/or to memory 410 for purposes of fingerprint analysis. As described in more detail below with reference to FIG. 6 and FIG. 7, medical device 400 may execute (or control the execution of) one or more fingerprint-secured operations, and security module 426 may represent the processing logic and intelligence that performs fingerprint analysis and other functions associated with the regulation of fingerprint-secured operations.

Function disable/enable module 428 may be used to selectively disable and enable functions, features, or operations of medical device 400 as needed. Alternatively (or additionally), function disable/enable module 428 may be used to selectively disable and enable functions, features, or operations of a device that is remotely controlled by medical device 400. If medical device 400 includes fingerprint reader 406 and fingerprint-linked security features, then function disable/enable module 428 could be utilized to unlock or lock fingerprint-secured operations as appropriate. Moreover, in a system deployment having multiple therapy delivery devices and/or multiple controller devices (see FIG. 1, FIG. 4, and related descriptions), function disable/enable module 428 can be used to coordinate, manage, and regulate control commands in the system. The relevance of function disable/enable module 428, and the manner in which medical devices handle control commands, will be discussed in more detail below with reference to FIGS. 13-20.

Data sync module 430 may be used to synchronize device and user data 454 at medical device 400. In this regard, physiological characteristic data, patient data, device status data, user preference data, device configuration settings, historical data, predictive data, and other types of data generated or otherwise processed by one device (such as a controller device or a therapy delivery device) may need to be shared with medical device 400. In a system deployment having multiple therapy delivery devices and/or multiple controller devices (see FIG. 1, FIG. 4, and related descriptions), synchronization of such data among the various system devices might be important to ensure consistent and non-conflicting behavior. Data sync module 430 can be suitably designed to determine whether or not device and user data 454 is synchronized, to synchronize if necessary, and/or to take other action as appropriate. The relevance of data sync module 430, along with associated synchronization techniques, are described in more detail below with reference to FIGS. 13-20.

Tracking module 432 was mentioned briefly above with reference to advertisement server module 418. Tracking module 432 is suitably configured to determine when a replenishable, refillable, maintainable, or replaceable item (such as a consumable) associated with medical device 400 needs to be replenished, refilled, maintained, replaced, etc. In this regard, tracking module 432 can monitor a remaining quantity, supply, inventory, an amount, a maintenance schedule, a timer, or any other measurable or detectable characteristic of the item to determine whether or not that item needs to be replenished, replaced, or maintained. In certain embodiments, tracking module 432 automatically determines when a consumable associated with medical device requires replacement or replenishment by analyzing device and user data 454. In the context of an infusion system, a consumable may be, without limitation: a medication such as insulin; a fluid reservoir, such as an insulin reservoir for an insulin infusion pump; an infusion set for an infusion pump; blood glucose meter test strips; blood glucose meter lancets; or a physiological characteristic sensor, such as a glucose sensor. A consumable may also be associated with the operation of the medical device itself. For example, a consumable may be, without limitation: a subscription to a remote monitoring service; additional increments of service time (e.g., a month of monitoring service); ring tones; wallpaper images; or the like.

In some embodiments, tracking module 432 determines a need to acquire a consumable product, item, or goods associated with operation of medical device 400. Alternatively (or additionally), tracking module 432 may determine a need to acquire something that is associated with treatment, diagnosis, or management of the patient's medical condition. In this regard, tracking module 432 could analyze device and user data 454 to determine whether the monitored medical condition requires attention. For example, if medical device 400 is part of an insulin infusion system, then tracking module 432 could monitor the glucose level of the patient and take action when it detects a glucose level that is not within the patient's normal range. In turn, tracking module 432 could influence advertisements or e-commerce features at medical device 400, where such advertisements or e-commerce features are associated with goods and/or services related to treatment of the medical condition. The relevance of tracking module 432 is described in more detail below with reference to FIGS. 21-24.

E-commerce module 434 is associated with a number of e-commerce, electronic transaction, and remote ordering features and functions of medical device 400. In preferred embodiments, e-commerce module 434 is operatively coupled to tracking module 432; this allows tracking module 432 to influence e-commerce at medical device 400. For example, e-commerce module 434 could initiate an order of a replenishable item when tracking module 432 determines that the replenishable items needs to be replenished. To accommodate internet-based electronic transactions, medical device 400 may include an appropriate web browser application 456, which could interact with e-commerce module 434. As is well understood by those familiar with online transactions, web browser application 456 can receive and present at least one web page that facilitates the completion of electronic orders for replenishable items, goods, services, or the like. The relevance of e-commerce module 434 is described in more detail below with reference to FIGS. 21-24.

Medical devices (e.g., a therapy delivery device, a controller device, or a therapy delivery device with integrated controller functionality) and medical device systems as described herein can support a number of features and operations that enhance the functionality of the medical devices and/or enhance the user experience of the medical devices. Unless otherwise noted, the description of these features and operations can apply generally to a therapy delivery device, a controller device, or a combined therapy/controller device. The following sections include descriptions of various processes and methods that may be performed by a medical device or by the medical device system. The various tasks performed in connection with a given process may be performed by software, hardware, firmware, or any combination thereof. For illustrative purposes, a process might be described with reference to elements mentioned above in connection with FIGS. 1-5. In practice, portions of a given process may be performed by different elements of the described system, e.g., a specified medical device, a remote server element, or an operating module or component of a medical device. It should be appreciated that a described process may include any number of additional or alternative tasks, the tasks included in a particular flow chart need not be performed in the illustrated order, an embodiment of a described process may omit one or more of the illustrated tasks, and a given process may be incorporated into a more comprehensive procedure or process having additional functionality not described in detail herein.

Fingerprint-Linked Control

A medical device as described herein may be suitably configured to support fingerprint-secured or fingerprint-linked operations. Such fingerprint related functions may involve, for example, fingerprint reader 222 (FIG. 2), fingerprint reader 236 (FIG. 3), fingerprint reader 406 (FIG. 5), security module 426 (FIG. 5), and possibly other components and/or modules of the medical device. The medical device can use fingerprint recognition techniques to verify a user, and also link a particular command, action, operation, or function to one or more fingerprints.

Figure 6:
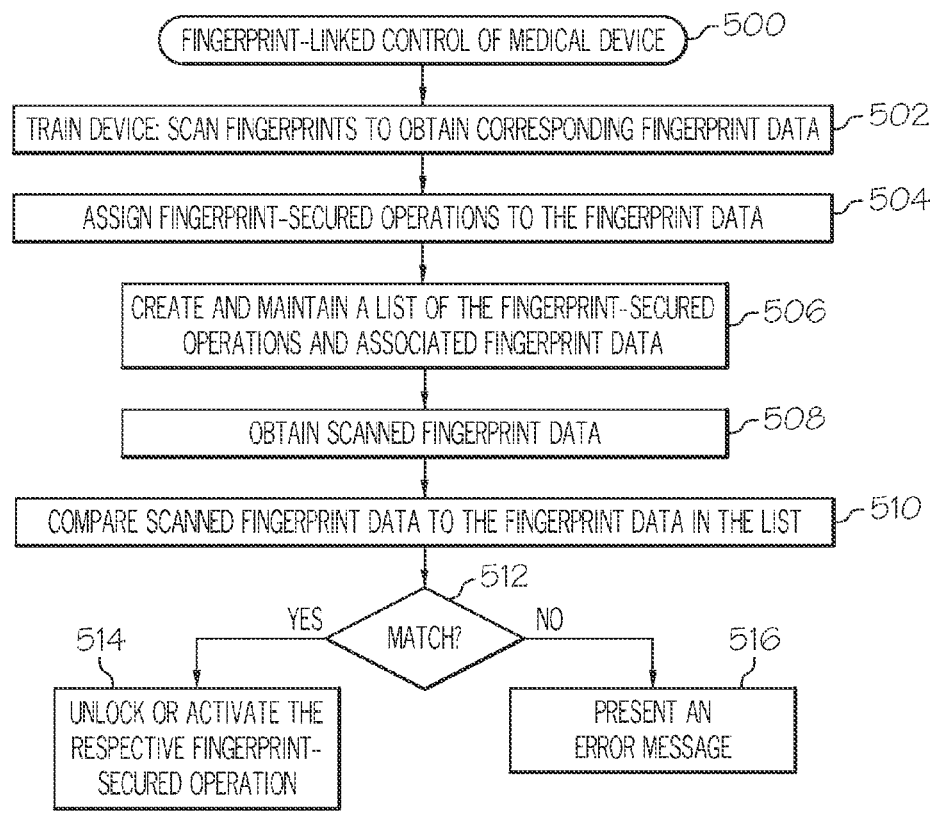
FIG. 6 is a flow chart that illustrates an embodiment of a fingerprint-linked control process suitable for use with a portable medical device.

FIG. 6 is a flow chart that illustrates an embodiment of a fingerprint-linked control process 500 suitable for use with a portable medical device. Process 500 can be performed to operate the medical device in a secure manner. For simplicity, process 500 includes several tasks that are related to the setup and initialization of the medical device. For example, the medical device may need to be trained before it can carry out fingerprint-linked operations. In this regard, process 500 can train the medical device by swiping fingerprints (task 502) to obtain corresponding fingerprint data, and then assign (task 504) certain fingerprint-secured or fingerprint-linked operations to respective fingerprint data. Thereafter, process 500 can create and maintain (task 506) an appropriate list of fingerprint-secured or fingerprint-related operations, along with their associated fingerprint data. This list of fingerprint-linked operations can be stored and maintained in the local memory element of the medical device.

Task 504 can assign the operations in any desired manner. For example, after swiping a single fingerprint, task 504 could allow the user to select an operation that will be linked to that particular fingerprint. Task 504 could also allow the user to identify the fingerprint by name, relationship, or otherwise. For a combination of at least two fingerprints swiped in sequence, task 504 may prompt the user to swipe the sequence of fingerprints before presenting the option to select and assign the operation to that particular combination of fingerprints. Thus, the list of fingerprint-secured operations could contain ten different operations, each being associated with a different fingerprint (as used here, a thumbprint is also considered to be a fingerprint) of one person. A list could also include fingerprint-secured operations associated with fingerprints of different people. Moreover, the list could associate the same fingerprint-secured operation to two different fingerprints (which may be taken from the same or different people). A one-to-multiple association like this might be desirable to allow the patient and a caregiver to control the same function using different fingerprints. In another deployment, the medical device could be configured to control delivery of therapy to a first patient (via a first therapy delivery device) and to control delivery of therapy to a second patient (via a second therapy delivery device), where the various therapy delivery operations are secured by different fingerprints.

Although a medical device could be suitably configured to support any number of different fingerprint-related operations, the embodiments described here maintain a list that contains therapy delivery operations linked to respective sets of identifiable fingerprint data, a list that contains display setting operations linked to respective sets of identifiable fingerprint data, and/or a list that contains menu selection operations linked to respective sets of identifiable fingerprint data. Different therapy delivery operations cause the medical device to deliver or administer different types or amounts of therapy to the patient (via the medical device itself or via a therapy delivery device under the control of the medical device). For example, one fingerprint-secured operation might correspond to the delivery of a first dosage of insulin, and another fingerprint-secured operation might correspond to the delivery of a second dosage of insulin. A display setting operation may cause the medical device to display a respective visual display, e.g., a chart, a graph, or the like. Thus, different fingerprints can be used to switch the display of the medical device. A menu selection operation may cause the medical device to display a respective menu, e.g., the home menu, a settings menu, a therapy programming menu, or the like. Thus, commonly used menus can be fingerprint-coded to facilitate quick switching of menu screens.

Figure 7:
FIG. 7 is a table of entries corresponding to exemplary fingerprint-linked operations of a portable medical device.

FIG. 7 is a table of entries corresponding to exemplary fingerprint-linked operations of a portable medical device. In practice, the content of such a list will vary depending upon the medical device type, the desired operations, the number of users, and other practical factors. For example, in an insulin infusion system, the fingerprint-linked operations may correspond to different insulin boluses, dosages, insulin therapy schedules, or the like.

Notably, each fingerprint-secured operation may be associated with one fingerprint or with a combination of different fingerprints. The list of fingerprint data may be indicative of fingerprints taken from any number of different people, e.g., the patient, a caregiver, a parent, a teacher, or the like. Although a combination of fingerprints will usually be taken from the same person, this need not always be the case. This list of FIG. 7 includes four entries corresponding to different individual fingerprints from a first person: the right index finger; the right ring finger; the right thumb; and the right pinky finger. The right index finger is linked to the operation labeled Deliver Therapy 1, the right ring finger is linked to the operation labeled Deliver Therapy 2, and the right thumb is linked to the operation labeled Display Home Screen. Notably, the right pinky finger is also linked to the operation labeled Display Home Screen. Such redundant assignment of operations may be supported by an embodiment of the medical device.

The list also includes one entry corresponding to a single fingerprint from a second person: the left pinky finger. This entry is linked to the operation labeled Deliver Therapy 1. Thus, Delivery Therapy 1 can be initiated by the first person (using the right index finger) or by the second person (using the left pinky finger). The list also includes two entries that require a specific combination or sequence of fingerprints taken from the first person. The operation labeled Show Chart is linked to the combination of the left index finger and the left middle finger. The operation labeled Reset Device is linked to the combination of the left index finger and the right index finger. Although certain embodiments might support only a limited number of fingerprint-secured operations (such as five or ten), the actual number need not be limited.

After the medical device has been trained with swiped fingerprints, process 500 can secure the associated operations such that they can be activated or unlocked using subsequently swiped fingerprint data. For example, the medical device can obtain swiped fingerprint data (task 508) using a fingerprint reader located on the medical device (or using a fingerprint reader that communicates with the medical device). As mentioned previously, a touch screen display element or a devoted sensor element could serve as the fingerprint reader. The swiped fingerprint data can then be analyzed to compare the swiped fingerprint data to identifiable fingerprint data maintained in the list of fingerprint-related operations (task 510). If the swiped fingerprint data satisfies certain matching criteria (query task 512) for a respective set of identifiable fingerprint data, then process 500 can unlock or activate the corresponding fingerprint-secured operation (task 514). The operation could be activated at the medical device itself or, if the medical device is a remote controller, then the remote controller could wirelessly transmit a control message to the device under its control—upon receipt of the control message, the receiving device can then execute the designated operation. If, however, the swiped fingerprint data does not match any of the previously swiped and trained fingerprint data, then process 500 will keep all fingerprint-linked operations secured. In addition, process 500 may present an error message (task 516) or simply exit without taking any action.

Display Features

A medical device, such as an insulin infusion pump and/or a wireless controller for an insulin infusion pump, may include a number of display features that enhance the user experience, appearance of the device, and enable better user interaction with the device. These display features include, without limitation: panning or scrolling of graphs and charts; hyperlinks or shortcuts for navigation of menu screens; and user-customizable display settings.

Display panning techniques and functions may involve, for example, display element 404, HMI elements 408, graphics engine 412 (see FIG. 5), and possibly other components and/or modules of the medical device. In preferred embodiments, display panning can be utilized during the display of physiological characteristic data (such as glucose level data) to allow the user to view an extended range of the data without changing the scaling of the display. This preserves the slope characteristics of the charted data, and makes the displayed data easier to consistently monitor and interpret.

Figure 8:
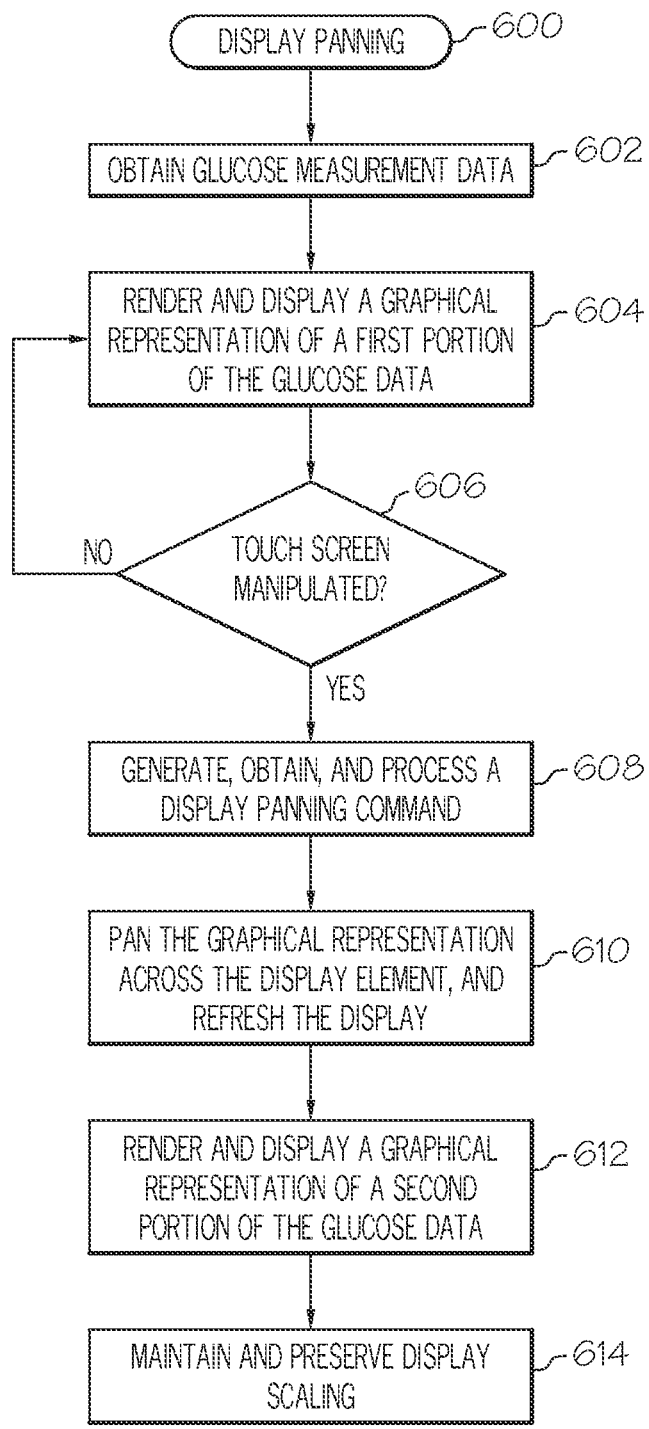
FIG. 8 is a flow chart that illustrates an embodiment of a display panning process suitable for use with a portable medical device.

FIG. 8 is a flow chart that illustrates an embodiment of a display panning process 600 suitable for use with a portable medical device, and FIGS. 9-12 are exemplary graphs of medical device data that is subjected to display panning. Although display panning can be used to adjust the display characteristics of any currently rendered screen on the medical device, this description relates to display panning for a graph of physiological characteristic data (specifically, the glucose level of a patient). It should be appreciated that the display panning techniques and methodologies can be extended to other displays, screens, and content. Process 600 can be performed to present an intuitive graphical display of patient data in a user-friendly manner.

Figure 9:
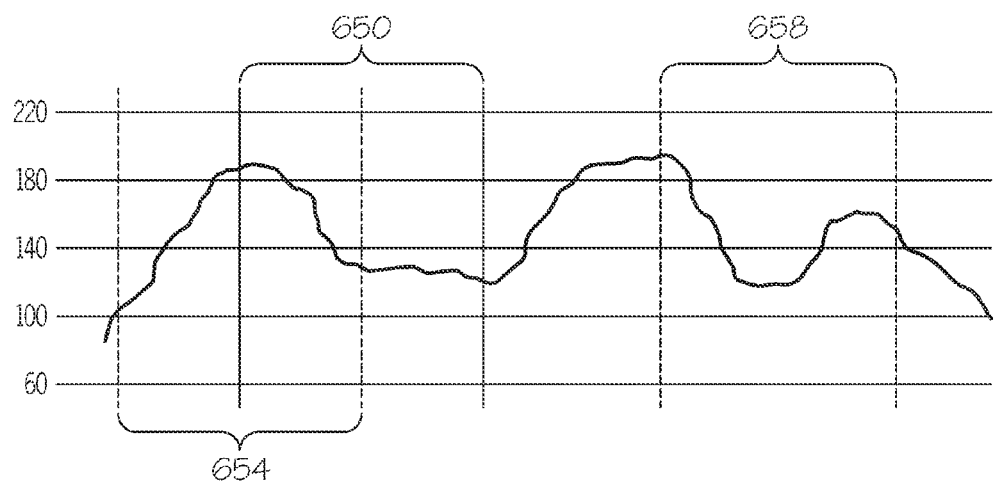
FIGS. 9-12 are exemplary graphs of medical device data that is subjected to display panning.

The illustrated embodiment of process 600 obtains measurement data corresponding to values of a physiological characteristic measured over a period of time, e.g., glucose measurement data (task 602). This data may be stored in the memory of the medical device so that it can be processed and rendered at the request of the user. FIG. 9 is an overall graph of glucose data collected over an arbitrary period of time, e.g., 16 hours. Although not depicted here, the data subjected to display panning may also include some predictive data, i.e., future data that is estimated based on historical data, trends, patient tendencies, etc.

Figure 10:
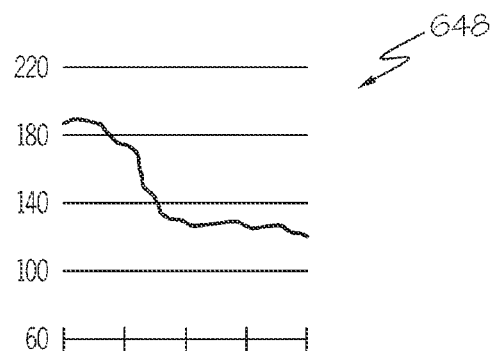

Process 600 can then render and display a graphical representation of a first portion of the glucose measurement data (task 604). Only a portion of the data shown in FIG. 9 might be displayed due to the limited physical size of the display element used by the medical device. In this regard, FIG. 10 shows a graph 648 of this first portion of data, using a horizontal scale of four hours. This first portion of data corresponds to a segment 650 of the overall graph depicted in FIG. 9. Accordingly, task 604 may result in a display of values measured during a first interval (four hours) of the overall period of time (16 hours). Notably, horizontal scaling is preserved, which results in the same slope characteristics for the displayed data. In addition, the vertical scaling remains the same—ranging from 60 to 220 in this example. In other words, the designated display scaling of FIG. 9 is carried over to FIG. 10.

The user of the medical device may want to view the glucose measurement data that is before or after the time interval shown in FIG. 10. The medical device can respond to a user manipulation of an HMI element or, in some embodiments, a touch screen display element, where such manipulation represents a panning command. In practice, the user could physically actuate a button, activate a displayed soft button, manipulate a pointing device, manipulate a touch pad, or manipulate a touch screen. Process 600 assumes that the medical device responds to manipulation of a touch screen display element. More specifically, if the first portion of the graph (shown in FIG. 10) is rendered on the touch screen display element, the user can touch and swipe over the screen to the left or right to control the panning of the displayed graph. If process 600 detects physical manipulation of the touch screen (query task 606) or some other HMI element, then an appropriate display panning command can be generated, obtained, and processed (task 608).

Figure 11:
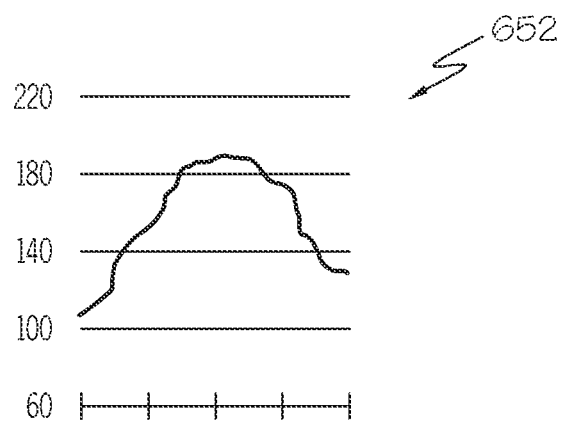

The display panning command causes the medical device to pan the graphical representation of the data across the display element, while updating and refreshing the displayed data (task 610). In preferred embodiments, such panning is performed in a smooth and continuous manner such that the user can perceive the graph moving across the display element. After completion of the panning operation, process 600 will render and display a graphical representation of a second portion of the overall glucose measurement data (task 612). In this regard, FIG. 11 depicts a graph 652 of this second portion of data, using the same horizontal scale of four hours. This second portion of data corresponds to a segment 654 of the overall graph depicted in FIG. 9. As depicted in FIG. 9, the time intervals associated with segment 650 and 654 overlap. Such overlapping is possible in preferred embodiments that accommodate dynamic panning in a virtually continuous manner.

Thus, for this example the graph 648 has been panned to the right, thus introducing "older" glucose measurement data on the left side of graph 652 and discarding "newer" glucose measurement data that had previously appeared on the right side of graph 648. In other words, at least a portion of graph 652 is not included in graph 648, and at least a portion of graph 648 has been removed from the display element. Notably, the glucose measurement data is rendered on the display element using fixed display scaling for both graph 648 and graph 652. In other words, the horizontal and vertical display scaling is preserved (task 614) during and after panning. Accordingly, although graph 648 and graph 652 convey values of the glucose level measured during different intervals of the overall period of time (see FIG. 9), each individual graph uses the same scaling and range of four hours.

Figure 12:
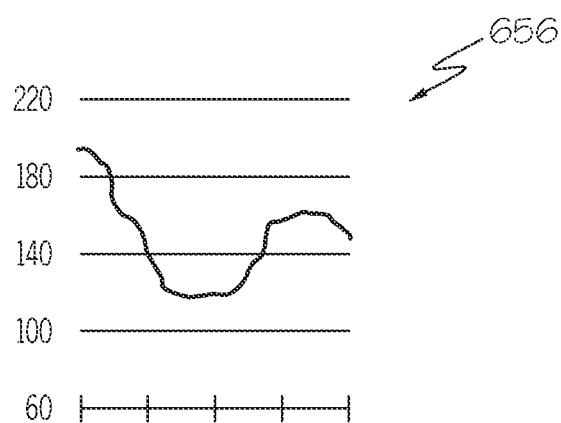

FIG. 12 depicts yet another graph 656 of a third portion of the overall glucose measurement data. This third portion corresponds to a segment 658 of the overall graph shown in FIG. 9. Unlike segment 650 and segment 654, this third segment 658 contains no overlapping data. For this example, the graph 656 represents the result of panning to the right, relative to graph 652. Due to the non-overlapping nature of graph 656, all of the information rendered in graph 652 has been discarded and replaced with different information. Referring again to FIG. 9, the panning feature allows the user to "grab and drag" the rendered graph and move it into the current viewing window that corresponds to the physical boundary of the display element.

The example provided here corresponds to dynamic panning along a time axis for the values of the measured physiological characteristic. Alternatively (or additionally), a display rendered by the medical device could be panned or scrolled along one or more other axes. For example, if the vertical resolution of the display element cannot accommodate the entire range of measured values, then the vertical axis of the rendered graphs could be panned while preserving the vertical scaling. Moreover, a touch screen implementation could accommodate panning in any direction. In other words, panning need not be restricted to the horizontal or vertical axes. In some touch screen implementations, multi-touch gestures could result in other adjustments to a displayed screen. For example, the medical device could support zooming in and out, display rotation, orientation adjustment, and switching of displays by detecting touching or movements of more than one finger.

As mentioned briefly above, the medical device could employ hyperlinks, hotkeys, or shortcuts to facilitate easy navigation and traversal of menu screens. Navigation of menu trees of older medical devices can be cumbersome and time consuming, especially if the menu structure is "linear" in nature, i.e., menus are navigated in a serial or sequential manner. Hyperlinks or shortcuts displayed on menu screens would allow the user to quickly jump to a home screen, to commonly used menu screens, or the like. Thus, even if a particular menu screen is nested rather deeply within a linear menu structure, a shortcut or hyperlink displayed on that particular menu screen would allow the user to easily return to another screen or menu. In practice, a menu shortcut could be linked to a button, a specified pattern or sequence of button presses, an active link that is displayed, a voice command, etc. Alternatively, a hyperlink may be displayed following an alarm, alert, or notification as a logical sequence to address or take action to the indicated state. For example, if the user receives a notification to calibrate their continuous glucose sensor, a hyperlink option would be provided on the notification screen to jump to the sensor calibration function.

As mentioned briefly above, the medical device could support user-customizable display settings that can be adjusted to personalize the look and feel of the medical device. For example, the medical device could support different display screen wallpapers, backgrounds, skins, or themes. Moreover, the medical device could support the use of personalized avatars, photographs, or other indicia of the patient or user. In addition to customizable display features, the medical device could support customizable sounds, alerts, ring tones, and alarms. Such customizable features may be desirable from a user standpoint even if they have little to no impact on the actual functionality of the medical device.

Coordination Between Multiple Devices

As mentioned previously with reference to FIG. 1 and FIG. 4, it may be necessary to provide techniques, protocols, and other measures to coordinate wireless communication between the various devices in a medical device system. A number of control command coordination processes will be described in this section; these processes are intended to address situations where conflicting, redundant, or concurrent control commands might be independently issued by multiple controller devices. These coordination processes may involve, for example, wireless module 420, function disable/enable module 428, data sync module 430 (see FIG. 5), and possibly other components and/or modules of the medical device.

Figure 13:
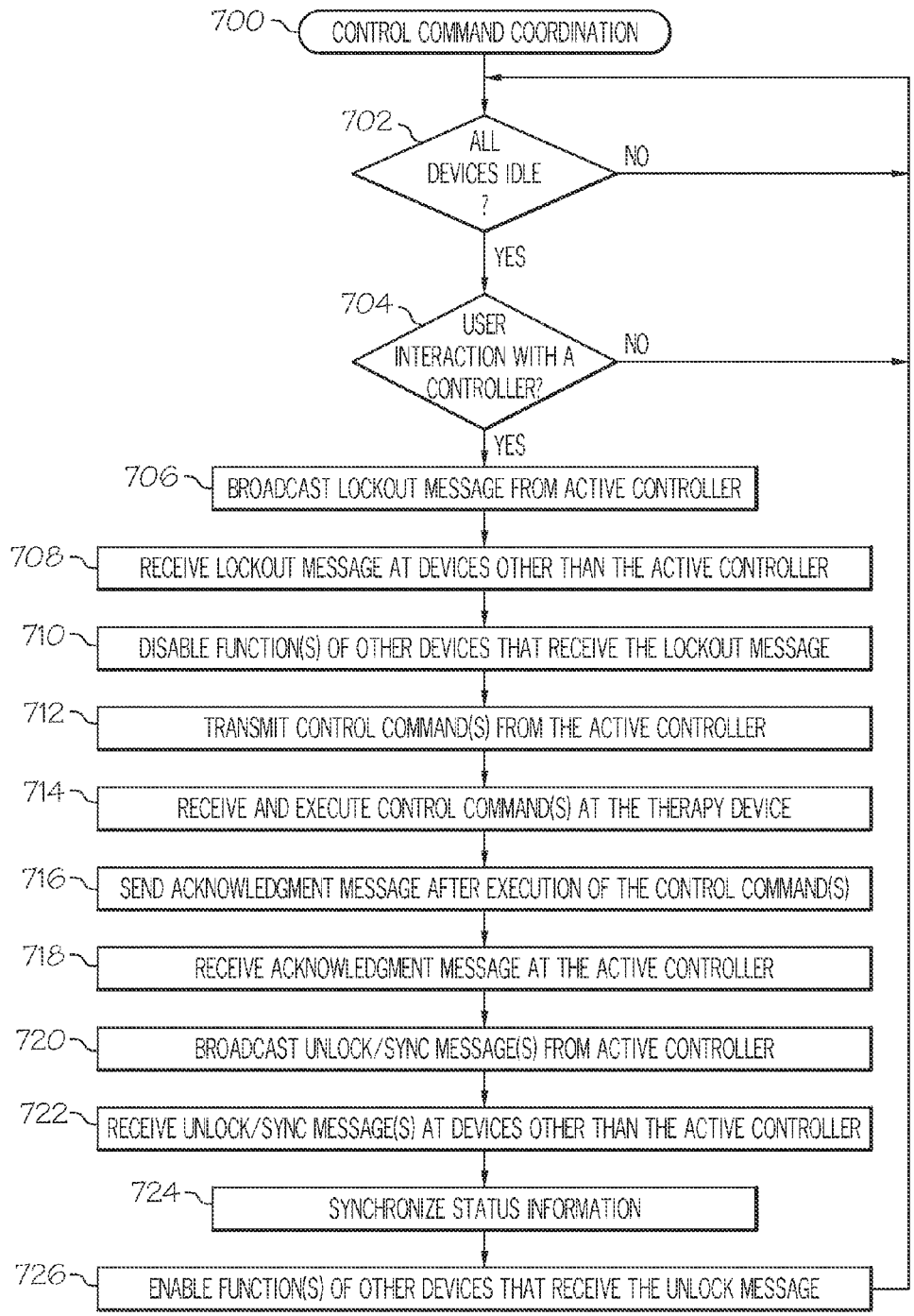
FIG. 13 is a flow chart that illustrates a first embodiment of a control command coordination process suitable for use with a medical device system.
Figure 14:
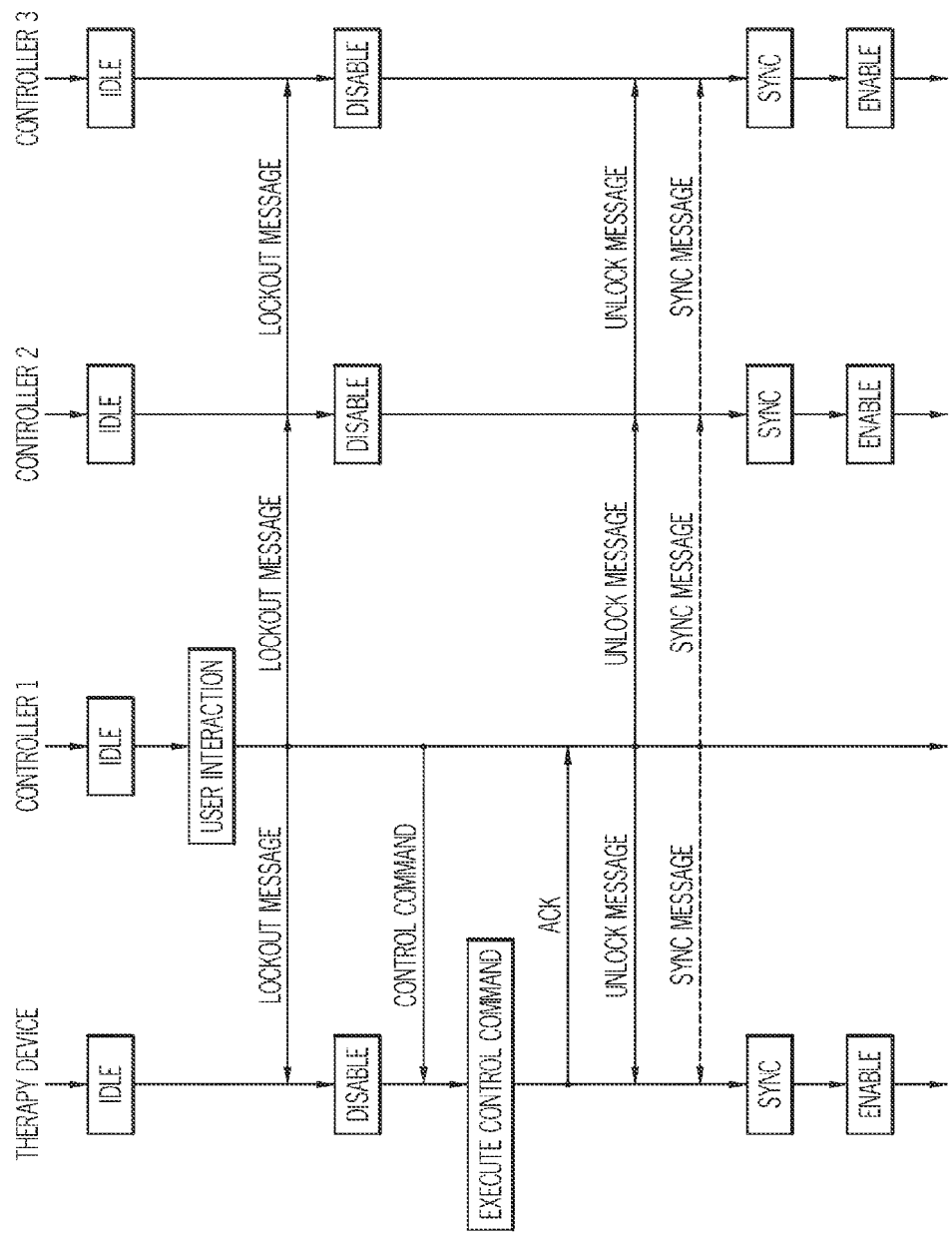
FIG. 14 is a message timing diagram corresponding to the control command coordination process shown in FIG. 13.

FIG. 13 is a flow chart that illustrates a first embodiment of a control command coordination process 700 suitable for use with a medical device system, and FIG. 14 is a message timing diagram corresponding to control command coordination process 700. As depicted in FIG. 14, this example assumes that one Therapy Device can be wirelessly controlled by three different controllers (labeled Controller 1, Controller 2, and Controller 3). The use of three controllers is representative of a multi-controller network; an embodiment of such a network need not be limited to any specific number of controllers. In FIG. 14, time is indicated by the vertical scale, with down indicating increasing time.

For this embodiment, all of the controller devices and the therapy device are maintained in a respective idle state or sleep mode when they are inactive. If all of the devices are in the idle state (query task 702), then process 700 continues because any one of the devices might be activated at any time to issue control commands. If, however, any one of the devices is active, then process 700 can assume that the active device is or will be issuing control commands. If process 700 detects some form of user interaction with one of the idle controller devices (query task 704), then process 700 continues. Otherwise, process 700 may be re-entered at an appropriate point, such as task 702. Regarding query task 704, each controller device can monitor itself to detect when user interaction occurs. Such user interaction may be associated with manipulation of an HMI element, engagement with a touch screen, motion detected by the controller device, a voice command detected by the controller device, or any action that causes the controller device to transition out of the idle state. Referring to FIG. 14, this example assumes that user interaction has been detected at Controller 1.

In response to the detected user interaction, the activated controller device wirelessly broadcasts a lockout (disable)

message (task 706). As explained in more detail below, the lockout message is broadcast in preparation of issuing a control command for the therapy device. This lockout message is suitably formatted and configured to disable at least one function of other controller devices and/or the therapy device upon receipt. In practice, the lockout message may convey a simple switching instruction that can be interpreted by any device that receives it, or it may convey specific information that is processed and acted upon by the receiving devices. The actual content and format of the lockout message can vary from one system to another, depending upon the specific needs and the deployment environment. FIG. 14 depicts Controller 1 broadcasting a lockout message, which is received by the Therapy Device, Controller 2, and Controller 3.

Process 700 assumes that the lockout message is wirelessly received by at least one other device other than the active controller (task 708). Again, FIG. 14 assumes that all of the other devices successfully receive the lockout message. Each device that receives the lockout message can process the lockout message and take appropriate action. More specifically, the lockout message causes the device to disable at least one of its functions, resulting in at least one disabled function (task 710). FIG. 14 depicts the disabling of the Therapy Device, Controller 1, and Controller 3 as a result of the lockout message. Some embodiments take a conservative approach and disable all functions of the device. Alternate embodiments may only disable functions that control, affect, or otherwise influence the delivery of therapy to the patient, while leaving less critical functions enabled. For example, even though therapy delivery, therapy programming, and therapy scheduling functions may be disabled at a given device, it might be desirable to keep other features enabled (e.g., display features, features unrelated to the medical needs of the patient, and certain alarm or alert features). If a controller attempts to enter the network during a lockout period, then it may be instructed to idle or wait until the lockout period is over. Alternatively, the new controller could be allowed to enter the network, while being immediately locked out thereafter.

After broadcasting the lockout message, the active controller can wirelessly transmit a control command to the therapy device (task 712). The control command is suitably formatted and configured to control one or more functions of the therapy device upon receipt of the control command at the therapy device. Process 700 assumes that the control command is successfully received and executed at the therapy device (task 714). FIG. 14 shows the control command being sent from Controller 1 to the Therapy Device, which thereafter executes the control command. The control command may be associated with any feature, function, operation, or method performed by the therapy device, including any feature, function, operation, or method described herein. For example, the control command may cause the therapy device to administer a particular bolus or dosage of insulin to the patient.

In the illustrated embodiment, the therapy device sends an acknowledgement message after it executes the control command (task 716). The acknowledgement message indicates that the control command was executed by the therapy device. The acknowledgement message may be broadcast or it may be intended only for the active controller. Process 700 assumes that the active controller receives the acknowledgement message (task 718). In this regard, FIG. 14 depicts the acknowledgement message being successfully transmitted from the Therapy Device to Controller 1. In response to the acknowledgement message, the active controller can wirelessly broadcast an unlock (enable) message (task 720). Process 700 assumes that the unlock message is received at the devices other than the active controller, including the therapy device and all other controllers (task 722). FIG. 14 depicts the broadcasting and receipt of the unlock message. This unlock message is suitably formatted and configured to clear or override the previously issued lockout message upon receipt of the unlock message at the other devices. In other words, the unlock message serves to re-enable the previously disabled functions.

In certain embodiments, the active controller may also broadcast a synchronization message that conveys synchronization data. The synchronization message may be broadcast separately, or it may be broadcast with the unlock message (or the unlock message may include the synchronization data). The synchronization data facilitates synchronizing of status information among the various devices in the system. FIG. 14 depicts the broadcasting and receipt of the synchronization message (the dashed lines in FIG. 14 represent the optional nature of a separate synchronization message).

In response to the synchronization data conveyed in the unlock message (or in the synchronization message), process 700 will synchronize the status information among the system devices (task 724). Referring to FIG. 14, the status information of the Therapy Device, Controller 2, and Controller 3 will be synchronized with the status information of Controller 1 (the active device). This synchronization step ensures that all of the devices in the system are aware of the recently executed control command, which was initiated by the active device (Controller 1). Notably, process 700 will also enable the previously disabled functions upon receipt of the unlock message at the devices other than the active controller (task 726). FIG. 14 depicts the enabling of the Therapy Device, Controller 2, and Controller 3. After re-enabling the devices in this manner, process 700 may exit or it may be re-entered at an appropriate point, such as task 702.

Notably, process 700 ensures that only one controller device can issue a control command to the therapy device. The lockout message temporarily disables the other controller devices, which prevents them from inadvertently issuing conflicting, redundant, or concurrent control commands. In practice, the devices in the system could implement procedures (e.g., conflict resolution, queuing, etc.) to handle the unlikely situation where two or more controllers simultaneously issue control commands. In such a scenario, the therapy device will resolve the race condition in an appropriate manner to ensure that only one controller is designated as the active controller.

Figure 15:
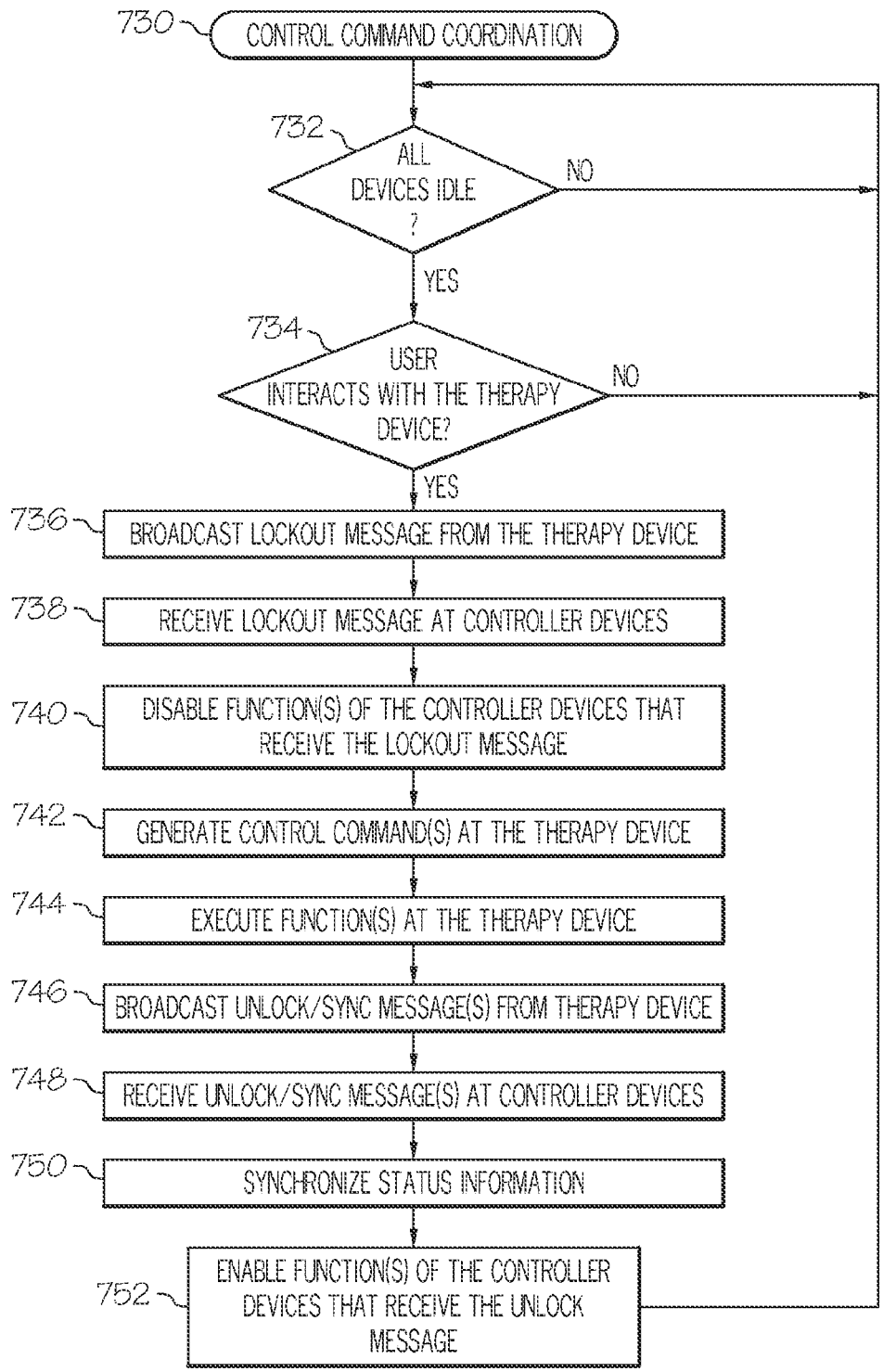
FIG. 15 is a flow chart that illustrates a second embodiment of a control command coordination process suitable for use with a medical device system.
Figure 16:
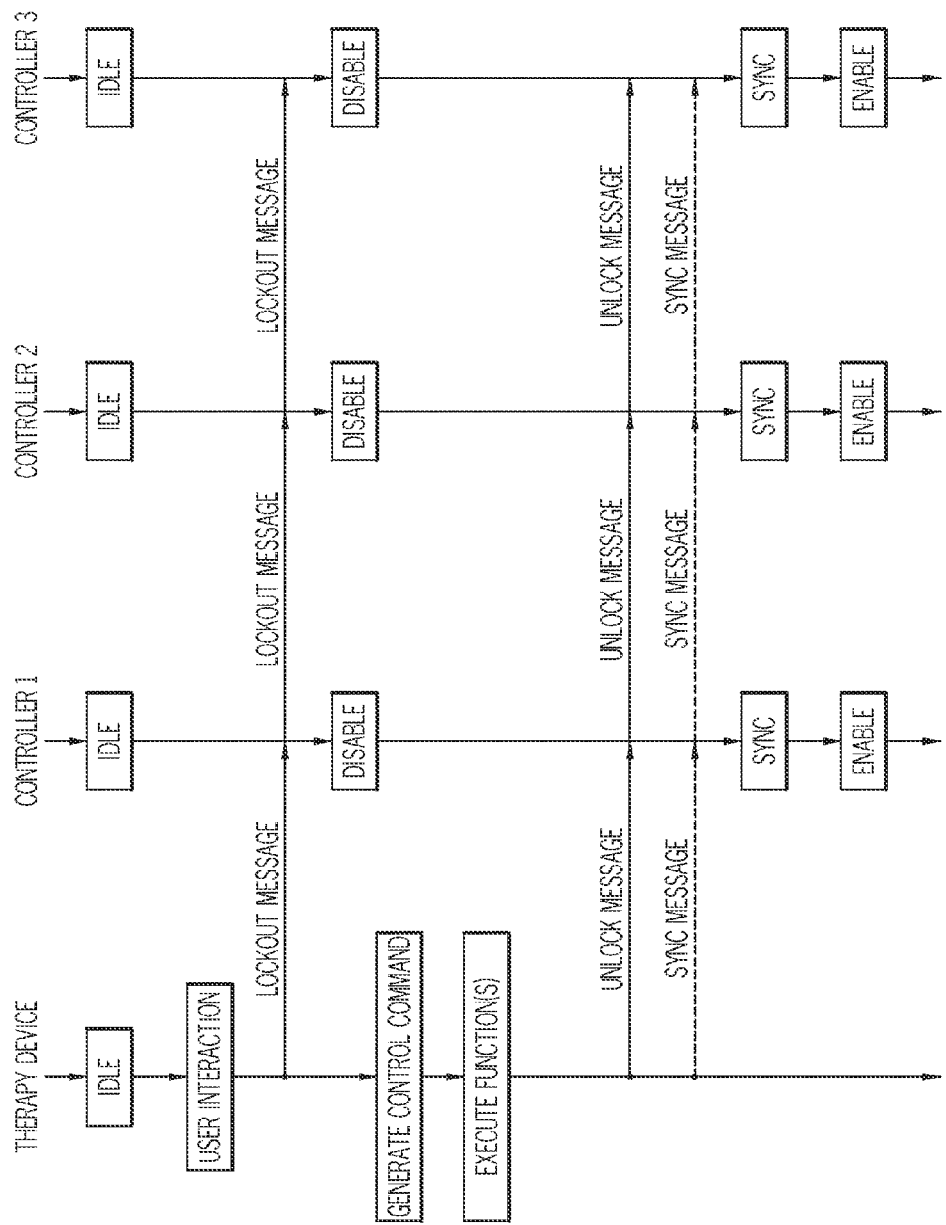
FIG. 16 is a message timing diagram corresponding to the control command coordination process shown in FIG. 15.

FIG. 15 is a flow chart that illustrates a second embodiment of a control command coordination process 730 suitable for use with a medical device system, and FIG. 16 is a message timing diagram corresponding to control command coordination process 730. Process 730 assumes that the therapy device includes native controller functionality, which enables a user of the therapy device to control at least some of its functions. As depicted in FIG. 16, this example assumes that one Therapy Device can be wirelessly controlled by three different controllers (labeled Controller 1, Controller 2, and Controller 3). In FIG. 16, time is indicated by the vertical scale, with down indicating increasing time. A number of the tasks, operations, and features of process 730 are similar, equivalent, or identical to counterparts described above with reference to process 700. For the sake of brevity, common subject matter will not be redundantly described here for process 730.

Process 730 is similar to process 700 in that it also checks whether all of the devices are in an idle state (query task 732). Unlike process 700, however, process 730 detects some type of user interaction at the therapy device rather than at one of the controllers (query task 734). FIG. 16 depicts the situation where user interaction has been detected at the Therapy Device. In response to detected user interaction, the therapy device wirelessly broadcasts a lockout (disable) message (task 736), which is received by one or more of the controller devices in the system (task 738). In contrast, the active controller device in process 700 issues the lockout message. FIG. 16 depicts the Therapy Device broadcasting a lockout message, which is received by Controller 1, Controller 2, and Controller 3.

The received lockout message disables at least one function of the controller devices (task 740). FIG. 16 depicts the disabling of Controller 1, Controller 2, and Controller 3 as a result of the lockout message. After broadcasting the lockout message, the active therapy device may generate an internal control command that is intended to prompt or initiate execution of one or more functions at the therapy device (task 742). In practice, the internal control command may be generated or issued after a slight delay to ensure that the controller devices have been disabled and/or to provide time for the therapy device to resolve any outstanding command conflicts or timing problems. The therapy device can then execute or perform the function(s) associated with the generated control command (task 744). FIG. 16 shows the control command being generated and executed by the Therapy Device. Notably, these tasks are performed while the controller devices are disabled.

After execution of the commanded function or functions, the therapy device wirelessly broadcasts an unlock message (which may include a synchronization message), which is intended for receipt by the disabled devices (task 746). As described above for process 700, a separate synchronization message could also be broadcast after execution of the commanded function or functions. Task 748 of process 730 assumes that all of the disabled devices receive the unlock/synchronization message(s). Moreover, FIG. 16 depicts the broadcasting and receipt of unlock and synchronization messages. In response to synchronization data conveyed in the unlock message and/or in the synchronization message, process 730 synchronizes the status information among the system devices (task 750). In particular, task 750 synchronizes the disabled controllers with the current device status data of the therapy device. FIG. 16 illustrates how Controller 1, Controller 2, and Controller 3 are synchronized. Process 730 will also enable the previously disabled functions of the controller devices upon receipt of the unlock message by the controller devices (task 752). FIG. 16 depicts the enabling of Controller 1, Controller 2, and Controller 3. After re-enabling the devices in this manner, process 730 may exit or it may be re-entered at an appropriate point, such as task 732.

Notably, process 730 ensures that the therapy device can issue control commands for itself, while preventing or ignoring conflicting commands that might be issued by a controller device. The lockout message temporarily disables the controller devices, which prevents them from inadvertently issuing conflicting, redundant, or concurrent control commands.

Figure 17:
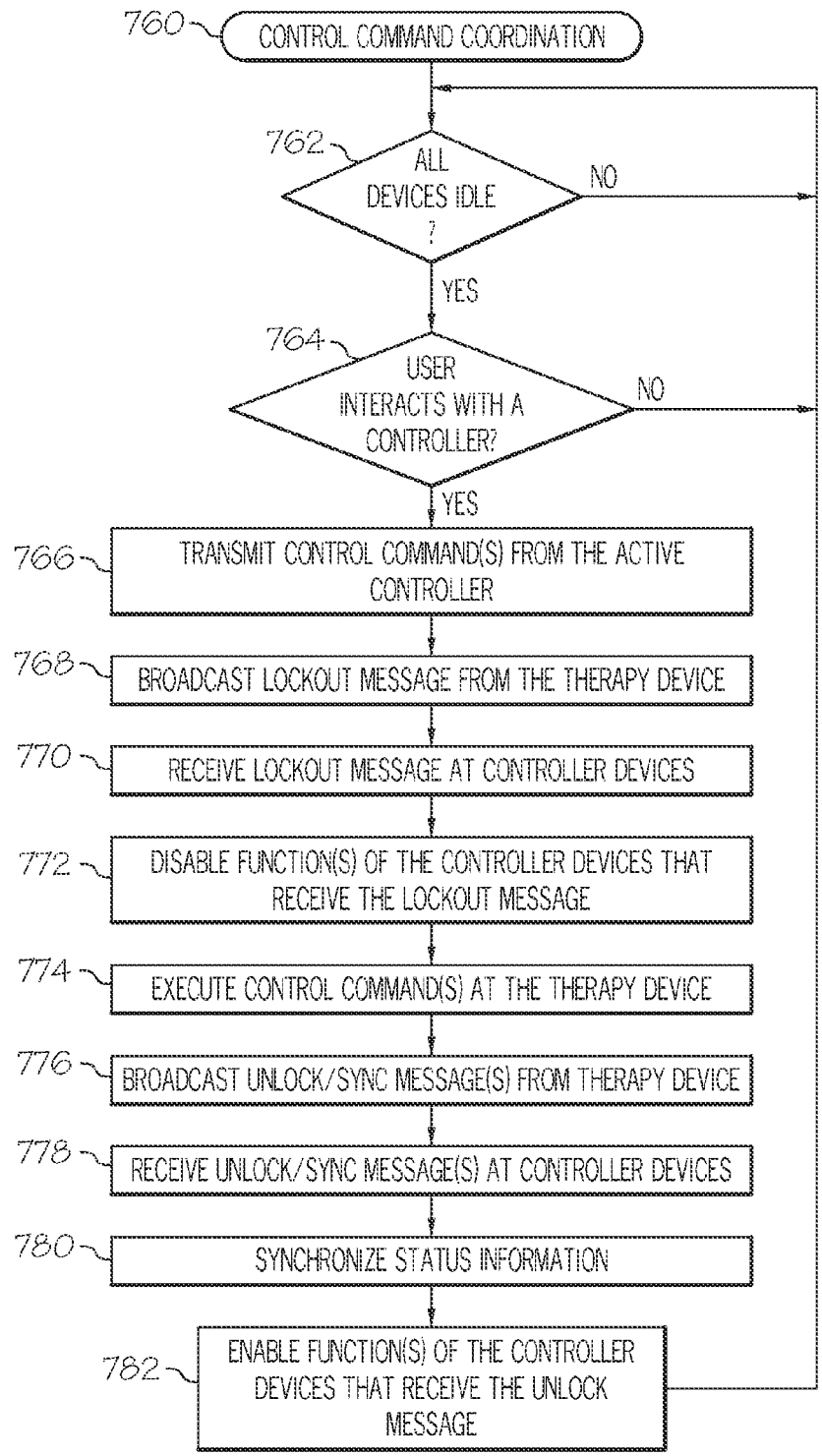
FIG. 17 is a flow chart that illustrates a third embodiment of a control command coordination process suitable for use with a medical device system.
Figure 18:
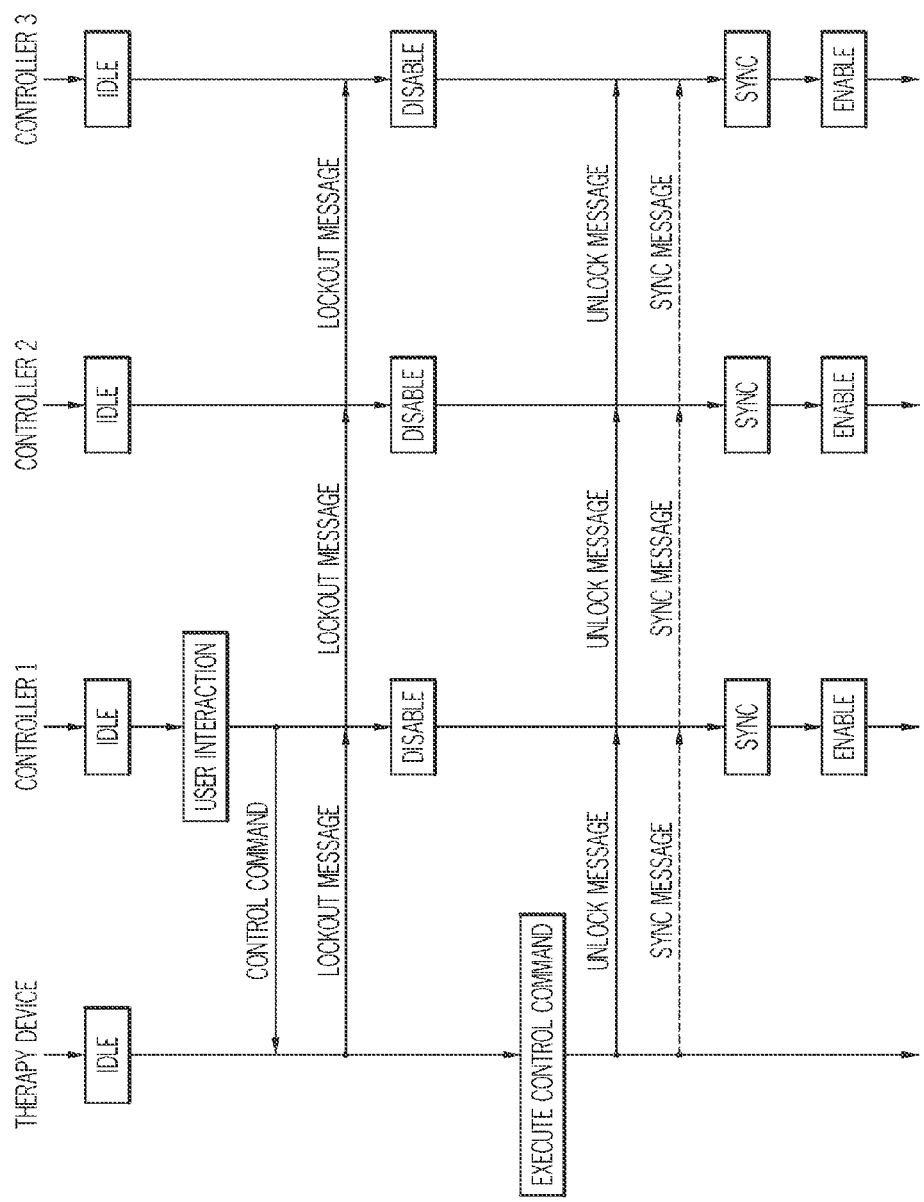
FIG. 18 is a message timing diagram corresponding to the control command coordination process shown in FIG. 17.

FIG. 17 is a flow chart that illustrates a third embodiment of a control command coordination process 760 suitable for use with a medical device system, and FIG. 18 is a message timing diagram corresponding to control command coordination process 760. As depicted in FIG. 18, this example assumes that one Therapy Device can be wirelessly controlled by three different controllers (labeled Controller 1, Controller 2, and Controller 3). In FIG. 18, time is indicated by the vertical scale, with down indicating increasing time. A number of the tasks, operations, and features of process 760 are similar, equivalent, or identical to counterparts described above with reference to process 700. For the sake of brevity, common subject matter will not be redundantly described here for process 760.

Process 760 is similar to process 700 in that it also checks whether all of the devices are in an idle state (query task 762), and it also detects a form of user interaction at one of the controller devices (query task 764). FIG. 18 depicts the situation where user interaction has been detected at Controller 1. Unlike process 700, the active controller device does not broadcast the lockout message in response to the detected user interaction. Instead, the active controller device wirelessly transmits a control command to the therapy device (task 766). Process 760 assumes that the control command is successfully received at the therapy device, and FIG. 18 shows the control command being sent from Controller 1 to the Therapy Device. As described above, the control command is formatted and written to control at least one function of the therapy device.

In response to receiving the control command, the therapy device wirelessly broadcasts a lockout (disable) message (task 768), which is preferably received by all of the controller devices in the system (task 770). In contrast, the active controller device in process 700 issues the lockout message. FIG. 18 depicts the Therapy Device broadcasting a lockout message, which is received by Controller 1, Controller 2, and Controller 3. The received the lockout message disables at least one function of the controller devices (task 772). Notably, process 760 can disable the originating controller device (Controller 1 in FIG. 18) because the relevant control command has already been received by the therapy device. In this regard, FIG. 18 depicts the disabling of Controller 1, Controller 2, and Controller 3 as a result of the lockout message.

After broadcasting the lockout message, the therapy device can then process, execute, or perform the previously received control command (task 774) in an appropriate manner. In practice, the control command may be acted upon after a slight delay to ensure that the controller devices have been disabled and/or to provide time for the therapy device to resolve any outstanding command conflicts or timing problems. FIG. 18 shows the control command being executed by the Therapy Device. After execution of the commanded function or functions, process 760 continues as described above for process 730. In this regard, tasks 776, 778, 780, and 782 in process 760 are equivalent to the respective tasks 746, 748, 750, and 752 in process 730.

As described previously in this section, it may be important to keep components in the medical device system synchronized with each other. Synchronization ensures that each device consistently processes the same device status data, the same patient data, the same physiological characteristic data, etc. In this regard, FIG. 19 is a flow chart that illustrates an embodiment of a wireless synchronization process 800 suitable for use with a medical device system. For the sake of simplicity and ease of description, process 800 is described in the context of wireless communication between one therapy device and one controller device. It should be realized that process 800 can be extended for use with a medical device system having any number of devices.

Process 800 begins with the assumption that the therapy device and the controller device are in wireless communication with each other. In other words, they are within normal wireless operating range. Although not a requirement, the following description designates the therapy device as the "hub" or "master" or "coordinator" device, and designates the controller device as the "slave" or "secondary" or "end node" device. These exemplary designators are utilized for the sake of illustration, and are not intended to limit or otherwise restrict the scope of the embodiments described here.

Process 800 may involve the periodic or scheduled broadcasting or synchronization messages (task 802) by one of the two devices. For this particular embodiment, the therapy device broadcasts beacons according to a predetermined and defined time schedule, and the beacons include, convey, or represent the synchronization messages. Moreover, the synchronization messages are intended for receipt by the controller device. During normal wireless operation, beacons will be broadcast in certain designated time slots, and those time slots are known a priori by both the transmitting device and the receiving device.

Process 800 checks whether the devices have lost wireless connectivity (query task 804). For the embodiment described here, task 804 can be performed by the controller device, and task 804 determines when the controller device loses wireless connectivity with the therapy device. In practice, the controller device can assume that wireless connectivity is lost when at least one synchronization message (or beacon) is not successfully received in its designated time slot. Alternatively, the controller device could monitor an appropriate metric related to wireless connectivity, e.g., received signal strength, signal-to-noise ratio, data error rate, or the like. If process 800 determines that wireless connectivity is lost (query task 804), then it can disable at least one function of the controller device (task 806). For this particular example, task 806 is preferably performed by the controller device itself as part of a self-disabling procedure.

Soon after wireless connectivity is regained or reestablished (query task 808), the controller device will begin receiving synchronization messages from the therapy device (task 810). Once it begins receiving new synchronization messages, the controller device can determine that it missed at least one synchronization message (broadcast during the period of time when wireless connectivity was lacking). This description assumes that some or all of the synchronization messages will include updated synchronization data, which is currently maintained by the therapy device. As mentioned previously in this section, the synchronization data could be associated with the status of the therapy device, patient-related data, physiological characteristic data, the status of the medical device system, or the like. Upon receipt of the updated synchronization data, process 800 synchronizes the controller device with the therapy device. In other words, the relevant status data of the controller device is synchronized with the corresponding current status data of the therapy device. After synchronization is complete, the disabled function(s) of the controller device can be re-enabled (task 814). At this point, both devices will be synchronized and wirelessly communicating with each other.

FIG. 20 is a flow chart that illustrates an embodiment of a fourth embodiment of a control command coordination process 830 that is suitable for use with a medical device system. Process 830 relates to the processing of control commands at a wireless controller device that is configured to control the operation of a therapy device for a patient. A number of the tasks, operations, and features of process 830 are similar, equivalent, or identical to counterparts described above with reference to process 700. For the sake of brevity, common subject matter will not be redundantly described here for process 830.

Process 830 may begin by obtaining a user input at the wireless controller device (task 832). The user input, which may be associated with user interaction with an HMI element of the controller device, corresponds to a request to initiate a command that influences therapy delivered by the therapy device. For example, the user input may be linked to a bolus delivery command, a therapy programming adjustment, a therapy schedule change, or the like. In contrast, other user inputs do not necessarily influence therapy delivered by the therapy device. These non-influencing user inputs include, for example: requests to display historical patient data; requests to display non-critical device status data; requests to view user preference settings; or the like.

Due to the importance of therapy-related commands, process 830 preferably checks a synchronization status between the controller device and the therapy device (query task 834). As described above for process 800, the synchronization status could be verified by checking whether the controller device has missed any synchronization messages that are broadcast in accordance with an agreed upon schedule. This synchronization check may be performed in response to the user input, or it may be performed periodically as a background task regardless of user inputs. If the devices are synchronized, then process 830 can proceed to task 842 (described below). If, however, the devices are not synchronized, then process 830 prevents execution, initiation, or processing of the requested command (task 836). In practice, task 836 may cause the controller device to disregard, ignore, or disable the effect of the requested command. This safeguard is desirable to ensure that the controller device does not inadvertently issue a conflicting or redundant control command due to lack of synchronization with one or more other independently operating controller devices.

If the devices are not properly synchronized, then the requested command may be disregarded until the controller device receives one or more synchronization messages (task 838). As described previously in this section, a synchronization message preferably contains or conveys updated synchronization data that is maintained at a hub or coordinator device. In this example, the synchronization messages are sent by the therapy device (via periodic beacons or upon interrogation by the controller device). Thus, the updated synchronization data can be used to synchronize the controller device with the therapy device (task 840). This synchronization step makes the controller device current with the therapy device and, ideally, with all other controller devices in the medical device system. In connection with task 840, process 830 could confirm that the devices are properly synchronized (query task 834). After synchronization, the controller device transmits one or more control messages to the therapy device (task 842). The control message or messages correspond to the original requested command (task 832). Thus, an actionable or executable control command will be transmitted to the therapy device only when the controller device is synchronized with the therapy device.

Automated E-Commerce and Advertisement Serving

Devices in a medical device system as described here may be suitably configured to automatically detect when to perform certain functions, to learn usage habits or patterns of the users, to intelligently introduce features as needed based on user experience, and the like. For example, a therapy delivery device (e.g., an infusion pump such as an insulin infusion pump) or a controller device for a therapy delivery device could be suitably configured to initiate, perform, or introduce certain e-commerce features and functions when necessary, relevant, or useful to do so. In preferred embodiments, the e-commerce features are contextually related to the operation or status of the medical device, the operation or status of the medical device system, a medical condition of the patient, treatment of the patient, and/or the preferences of the patient or user. The device learning and e-commerce related processes and techniques may involve, for example, some or all of the following components and modules depicted in FIG. 5: display element 404; HMI elements 408; memory 410; GPS receiver 414; navigation module 416; advertisement server module 418; wireless module 420; tracking module 432; e-commerce module 434; and possibly other elements and/or modules of the medical device.

A system deployment could also allow the user to purchase, subscribe to, or otherwise participate in a remote monitoring service. In this regard, a healthcare professional or caregiver could actively monitor the patient and/or device status in a remote manner and provide recommendations as needed. The service could also accommodate remote programming and configuration of the patient's medical device if so desired.

Figure 21:
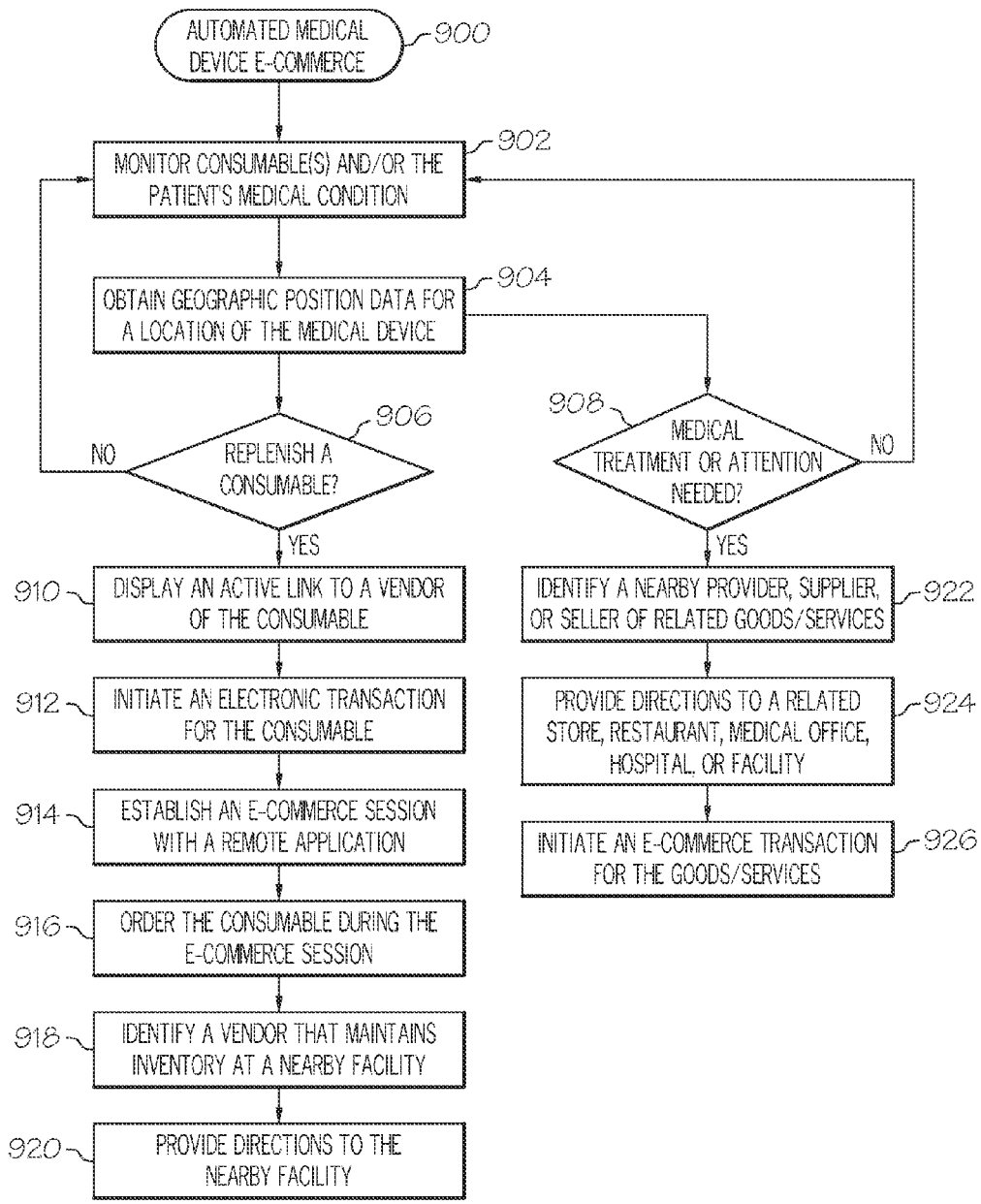
FIG. 21 is a flow chart that illustrates a first embodiment of an automated medical device e-commerce process suitable for use with a medical device system.

FIG. 21 is a flow chart that illustrates a first embodiment of an automated medical device e-commerce process 900 suitable for use with a medical device system. Process 900 may be associated with the operation of a therapy delivery device, a controller device, a monitor device, or some other component of a medical device system. Process 900 is associated with the delivery or presentation of e-commerce features, advertisements, or the like, in response to the detection of certain triggers or conditions. For example, process 900 may be utilized to carry out time-based release of advertisements, or the periodic pushing of advertisements from a remote server. As another example, process 900 can monitor certain conditions of the patient and/or a device within the medical device system, and use the monitored conditions as trigger criteria. The illustrated embodiment of process 900 monitors a status, a characteristic, a state, a condition, a quantity, a parameter, and/or any detectable, measurable, obtainable, or derivable indicator associated with at least one consumable and/or a medical condition of the patient (task 902). For example, tracking module 432 (see FIG. 5) could be used to monitor a consumable product, item, or component used by a therapy delivery device, to monitor device status data, and/or to monitor patient/user data. A monitored consumable may be a replenishable, replaceable, refillable, or maintainable item, such as, without limitation: a medication delivered by a therapy delivery device; an insulin reservoir of an insulin infusion pump; an infusion set used by an infusion pump; a physiological characteristic sensor, such as a glucose sensor; a battery used by a medical device; or an accessory used with a medical device. The medical device could also monitor physiological patient data, device usage data, historical data, and/or other data to determine whether the patient's medical condition requires attention, treatment, or diagnosis.

The exemplary embodiment described here obtains geographic position data that indicates a location of the medical device (task 904). The geographic position data may include or be realized as GPS data, and the GPS data could be obtained from a suitably configured onboard GPS receiver of the host medical device. In practice, the geographic position data is indicative of the current location of the medical device, and task 904 is preferably performed in an ongoing manner as a background task during active operation of the medical device. The relevance of the geographic position data is described in more detail below.

This particular version of process 900 automatically determines when a consumable associated with the medical device requires replenishment, replacement, maintenance, or the like (query task 906). In connection with this determination, process 900 could also indicate or recommend a quantity, number of units, volume, or amount of the consumable that might be required. Moreover, process 900 can automatically determine when the patient might need medical treatment, medical attention, a medical diagnosis, or the like (query task 908). The determinations associated with query tasks 906 and 908 could be made independently and concurrently at any time. Accordingly, FIG. 21 includes two separate paths for process 900. It should be appreciated that these two paths may be followed independently, sequentially, concurrently, or otherwise (as needed).

If query task 906 determines that a consumable needs to be replenished, replaced, maintained, or refilled, then process 900 may prompt an electronic transaction for that particular consumable. In some embodiments, the medical device displays an active link to a vendor, seller, or provider of the consumable (task 910). In this context, the active link may be a graphically rendered interactive element that can be activated or manipulated by the user of the medical device. For example, the active link may be a hyperlink, a soft button, an icon, or other element rendered on the display element of the medical device. In response to selection or manipulation of the active link, process 900 initiates an electronic transaction for the consumable (task 912). The electronic transaction may be associated with an online transaction, an electronic order, an internet-based transaction, a purchase order conveyed over a cellular telephone network, a web-enabled order, an e-commerce transaction, or the like. In this regard, the medical device may establish a wireless e-commerce session with a remote e-commerce application (task 914), which may reside at a network server, a remote computing device, or any location that is physically distinct from the medical device itself. In practice, task 914 may be associated with a data communication session (preferably a secure session) during which information can be transferred between the medical device and the remote e-commerce application.

The medical device or a user of the medical device can order an appropriate quantity, number of units, or amount of the consumable during the e-commerce session (task 916). For instance, during this session the e-commerce module of the medical device can cooperate with the remote e-commerce application to execute a purchase transaction for the consumable. In certain embodiments, the system supports user input that can filter or modify transactions or recommendations made by the medical device. For instance, the user might be allowed to purchase multiple items (which may or may not be suggested by the system, adjust quantities, only order the recommended item, etc.). In certain embodiments, the geographic position data obtained during task 904 is used to identify at least one provider, vendor, or seller of the item of interest (task 918), where the identified party (or parties) maintains an inventory of the item at a facility or store that is located within a predetermined distance from the present location of the medical device. Thus, the geographic position data can be used to guide the user of the medical device to a nearby storefront, office, or facility that carries the consumable product that is in need of replenishment or replacement. Moreover, the geographical position data could be processed to provide directions to the storefront, office, or facility (task 920). Notably, navigation guidance and directions to a facility will be influenced by the geographic position data and by the geographic location of the facility itself. The directions, guidance information, and/or a map could be rendered on the display element of the medical device, and the displayed information could be updated periodically or in substantially real-time in response to movement of the medical device. In certain embodiments, the geographic position data obtained during task 904 is used to support social networking features and applications. For example, the geographic position data could be used to locate and/or identify nearby users of compatible medical devices, and the compatible medical devices could support a variety of social networking applications (such as text messaging, chatting, games, etc.).

Referring to the second branch of process 900, if query task 908 determines that medical treatment, attention, or diagnosis should be recommended, then process 900 may analyze and process the geographic position data (obtained during task 904) to identify at least one provider, vendor, supplier, or seller of goods and/or services that are related to the medical condition or to treatment of the medical condition (task 922). Thus, process 900 can identify a provider of medical services, a physician, a hospital facility, a restaurant or convenience store that sells human nourishment (food and/or drink) that might be associated with treatment of the medical condition, a treatment facility, or the like. As mentioned above, process 900 could filter or limit the identified parties to those having a facility, office, or storefront that is located within a predetermined distance from the present location of the medical device. Moreover, the system may allow the user to interact with the medical device to filter or modify treatment transactions or recommendations made by the medical device.

In this embodiment, the geographical position data is also used to provide directions, a map, and/or navigation guidance to the store, restaurant, medical office, hospital, or facility of interest (task 924), as described above for the other branch of process 900. For example, if the patient is diabetic and the medical device detects a glucose level that is below a certain threshold level for the patient, then process 900 may identify a nearby restaurant or convenience store, and guide the patient to the restaurant or store. In addition, the medical device could prompt or initiate an electronic transaction for the desired goods and/or services (task 926), using the approaches described above for the other branch of process 900.

Figure 22:
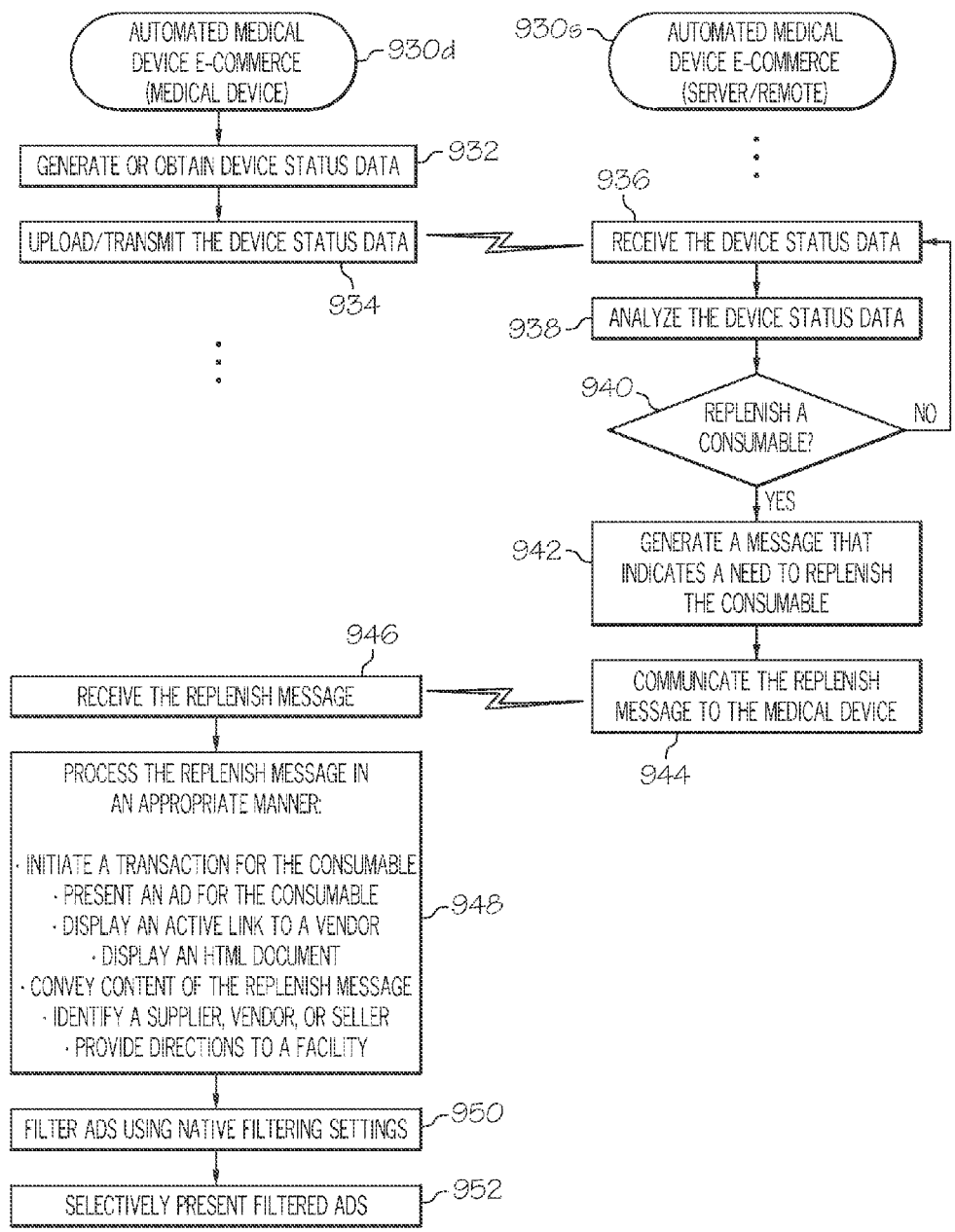
FIG. 22 is a flow chart that illustrates a second embodiment of an automated medical device e-commerce process suitable for use with a medical device system.

FIG. 22 is a flow chart that illustrates a second embodiment of an automated medical device e-commerce process 930 suitable for use with a medical device system. Process 930 is similar to process 900 described above, however, some of the decision-making intelligence resides at a remote element such as a server system or application. For this reason, the left side of FIG. 22 corresponds to tasks performed by the medical device (labeled process 930*d*), and the right side of FIG. 22 corresponds to tasks performed by the server application (labeled process 930*s*).

In connection with process 930, the medical device may generate, produce, or otherwise obtain device status data (task 932), where such status data indicates a remaining quantity, supply, inventory, or amount of a consumable used by the medical device. It should be realized that the device status data may be associated with operation of the medical device itself, or it may be associated with operation of another device that communicates with the medical device. For example, if the medical device is a wireless controller device, then the device status data may be related to operation of the controller device and/or related to operation of a therapy device under the control of the controller device.

Several examples of applicable consumables were mentioned above with reference to process 900. Thus, the status data obtained during task 932 may indicate a level of fluid remaining in a fluid reservoir, a remaining useful life of a physiological characteristic sensor, a remaining useful life of an infusion set, or the like. Process 930 assumes that the medical device is capable of uploading or otherwise transmitting the device status to a remote computing device or application that is physically distinct and separate from the medical device itself (task 934). Although not required, preferred embodiments upload the device status data using wireless data communication techniques. Process 930 also assumes that the device status data is successfully received at the remote server application (task 936). Upon receipt, the server application may analyze and process the device status data in an appropriate manner (task 938) to determine when a consumable associated with the medical device requires replacement, replenishment, maintenance, refilling, etc. This aspect of process 930 was described above with reference to process 900, and will not be redundantly described here.

If the server application determines that a consumable needs to be replenished (query task 940), then the server application can take appropriate action. Otherwise, the server application may continue monitoring the received device status data. When a consumable needs to be replenished or replaced, the server application may generate a message that indicates a need to replenish that particular consumable (task 942). In certain situations, this message may indicate or identify a quantity, number of units, volume, or amount of the consumable that might be required. This replenish message can then be communicated back to the medical device using any suitable data transmission scheme (task 944). Although not always required, preferred embodiments communicate the replenish message in a wireless manner.

The specific content, format, and configuration of the replenish message may vary from one deployment to another, and may vary as necessary to meet the needs of the particular application. For example, the replenish message may include an active link to a vendor, supplier, or seller of the consumable. As mentioned above with reference to process 900, an active link in this context facilitates the initiation of an electronic transaction for the consumable (at the medical device). In practice, the active link could be delivered via an email, a text message, an HTML document such as a web page, or the like. As another example, the replenish message may include or be associated with an advertisement for the particular consumable; the advertisement might identify an address, a business name, a telephone number, and/or other pertinent information related to the vendor, supplier, or provider of the consumable. As yet another example, the replenish message may be conveyed in a voicemail format by placing a telephone call to a telephone-enabled medical device, or it may be conveyed in an electronic media file (audio or video) that is transmitted to the medical device.

Process 930 assumes that the replenish message is successfully received by the medical device (task 946). The medical device can then process and respond to the replenish message in an appropriate manner (task 948). For example, the medical device can perform one or more of the following actions, without limitation: initiate an electronic transaction (or any form of transaction) for the consumable; present an advertisement for the consumable; display an active link to a vendor, seller, or provider of the consumable; display an HTML document, such as a web page that facilitates completion of a transaction for the consumable; convey content that is included in the replenish message; identify a vendor, seller, or provider of the consumable; or provide directions to a facility maintained by a vendor, seller, or provider. As mentioned above, the medical device might allow the user to filter or modify transactions or recommendations made by the medical device. For instance, the user might be allowed to purchase multiple items (which may or may not be suggested by the system, adjust quantities, only order the recommended item, etc.). In certain embodiments, the replenish message includes or conveys one or more advertisements, and the medical device is capable of filtering advertisements using native filtering settings (task 950). Such filtering allows the medical device to selectively present one or more of the advertisements, based on the filtering routine (task 952).

Thus, even if the server application sends multiple advertisements to the medical device, process 930 could implement filtering algorithms, user settings, or other logic that blocks certain advertisements and/or allows certain advertisements.

Figure 23:
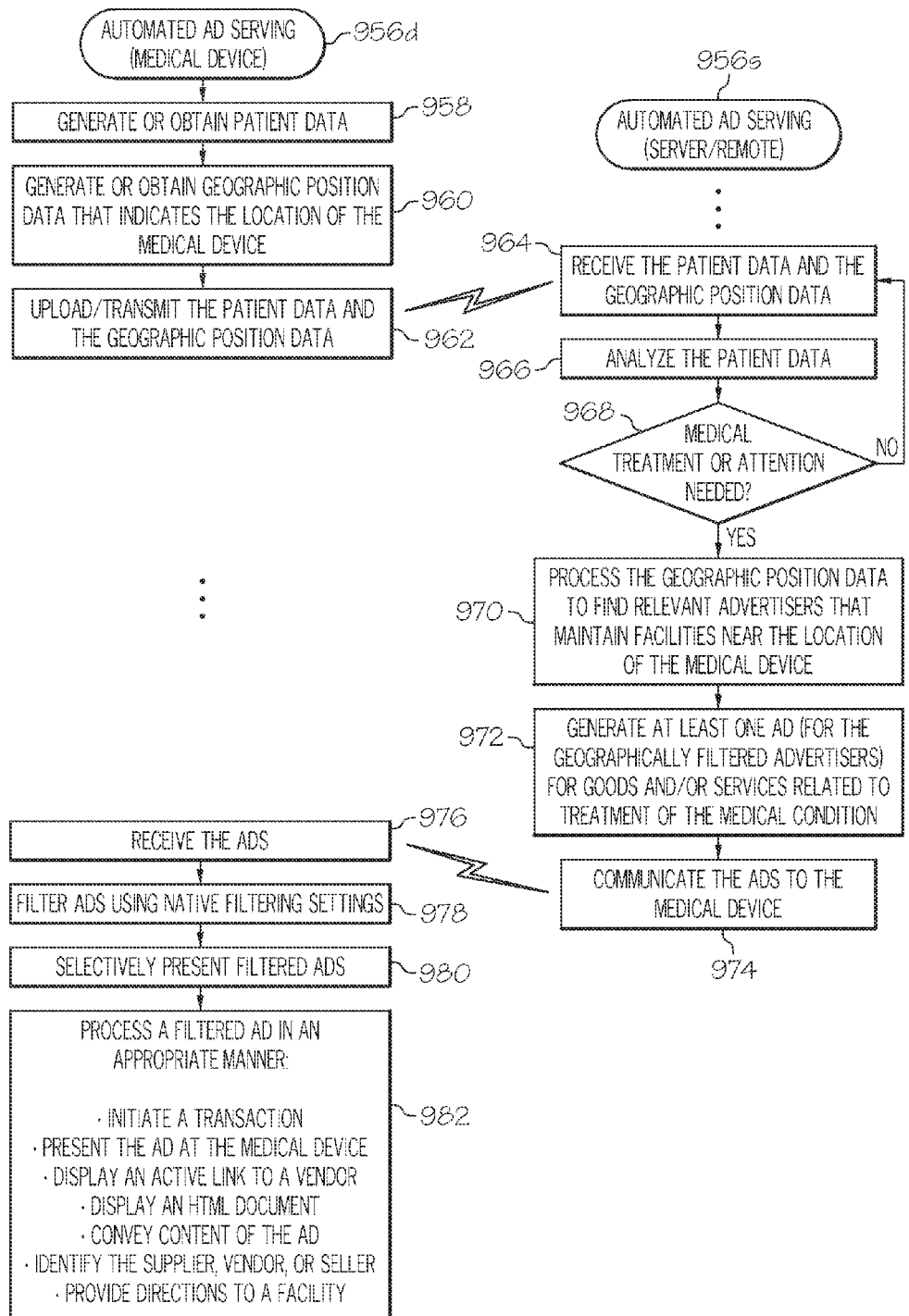
FIG. 23 is a flow chart that illustrates an embodiment of an automated advertisement serving process suitable for use with a medical device system.

FIG. 23 is a flow chart that illustrates an embodiment of an automated advertisement serving process 956 suitable for use with a medical device system. The left side of FIG. 23 corresponds to tasks performed by the medical device (labeled process 956*d*), and the right side of FIG. 23 corresponds to tasks performed by the server application (labeled process 956*s*). A number of the tasks, operations, and features of process 956 are similar, equivalent, or identical to counterparts described above with reference to process 900 or process 930. For the sake of brevity, common subject matter will not be redundantly described here for process 956.

In connection with process 956, the medical device may generate, produce, or otherwise obtain patient data (task 958), where such patient data is somehow associated with, descriptive of, or linked to a medical condition of a patient. It should be realized that the patient data may be associated with operation of the medical device itself, or it may be associated with operation of another device that communicates with the medical device. For example, if the medical device is a wireless controller device, then the patient status data may be related to operation of a patient monitor and/or related to operation of a therapy device that is under the control of the controller device.

The medical device may also generate or obtain geographic position data that indicates a location of the medical device (task 960). As mentioned previously, such geographic position data could be obtained from an onboard GPS receiver. This embodiment of process 956 continues by uploading or otherwise transmitting the patient data and the geographic position data to the remote computing device or application (task 962). Although not required, preferred embodiments upload the patient data and the geographic position data using wireless data communication techniques. Process 956 assumes that the patient data and the geographic position data is successfully received at the remote server application (task 964). The server application can then analyze and process the patient data in an appropriate manner (task 966) to determine whether when the medical condition of the patient requires attention, treatment, or diagnosis (query task 968). This aspect of process 956 was described above with reference to process 900, and will not be redundantly described here.

If the server application determines that medical treatment, diagnosis, or attention is necessary, then the server application can take appropriate action. Otherwise, the server application may continue monitoring the received patient data. When medical attention, treatment, or diagnosis is recommended, the server application processes the geographical position data to find relevant advertisers that maintain one or more facilities that are located within a predetermined distance from the medical device (task 970). In other words, the server application uses the geographic position data as filtering criteria to identify vendors, suppliers, or providers that are located near to the medical device and, presumably, near to the patient. In this regard, process 956 generates at least one advertisement for the geographically filtered advertisers (task 972), and the content of the advertisements will be influenced by the geographic position data. In preferred embodiments, these filtered advertisements are for goods and/or services that are somehow related to the treatment, diagnosis, cure, or research of the patient's medical condition. The generated advertisements can then be communicated back to the medical device using any suitable data transmission scheme (task 974). Although not always required, preferred embodiments communicate the advertisements in a wireless manner.

The specific content, format, and configuration of an advertisement, and the manner in which it is conveyed, may vary from one deployment to another, and may vary as necessary to meet the needs of the particular application. In practice, an advertisement could include or be associated with a text message, an HTML document such as a web page, an active link to a service provider, or the like. Moreover, an advertisement might identify an address, a business name, a telephone number, and/or other pertinent information related to the vendor, supplier, or provider.

Process 956 assumes that at least one advertisement is received by the medical device (task 976). The medical device can then filter the advertisements using native filtering settings (task 978), and selectively present one or more of the filtered advertisements (task 980). Thus, even if the server application sends multiple advertisements to the medical device, process 956 could implement filtering algorithms, user settings, or other logic that blocks certain advertisements and/or allows certain advertisements. The medical device can then process a filtered advertisement in an appropriate manner (task 982). For example, the medical device can perform one or more of the following actions, without limitation: initiate an electronic transaction (or any form of transaction) for the goods/services; present the advertisement at the medical device; display an active link to a vendor, seller, or provider of the goods/services; display an HTML document, such as a web page that facilitates completion of a transaction for the goods/services; convey the content of the advertisement; identify the supplier, vendor, seller, or provider of the goods/services; or provide directions to a facility maintained by the supplier, vendor, seller, or provider. As mentioned previously, the medical device can obtain user input that allows the user to filter or modify transactions or recommendations made by the medical device.

Figure 24:
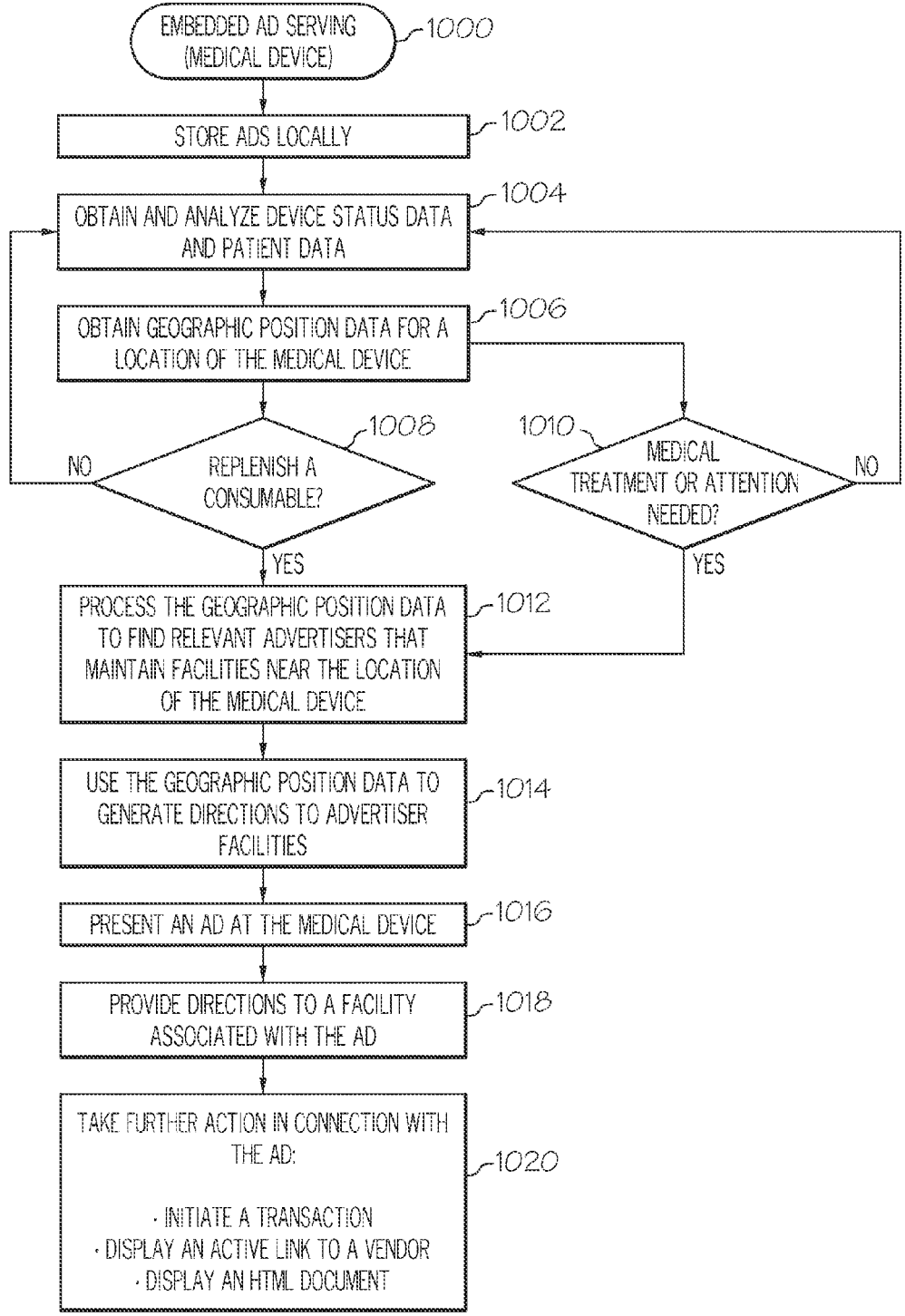
FIG. 24 is a flow chart that illustrates an embodiment of an embedded advertisement serving process suitable for use with a medical device system.

FIG. 24 is a flow chart that illustrates an embodiment of an embedded advertisement serving process 1000 suitable for use with a medical device system. A number of the tasks, operations, and features of process 1000 are similar, equivalent, or identical to counterparts described above with reference to process 900, process 930, or process 956. For the sake of brevity, common subject matter will not be redundantly described here for process 1000.

Process 1000 generally relates to a native and embedded process that can be implemented by an individual medical device, regardless of network connectivity, internet connectivity, or connectivity with another medical device in a system. Accordingly, the medical device stores advertisements locally (task 1002), and the advertisements may be preloaded by the manufacturer of the device, by the patient, by a physician, etc. A network-enabled medical device could receive advertisements from a remote application and store the advertisements locally. During process 1000, the medical device may obtain and analyze device status data (its own status data and/or the status data of another device) and/or patient data (task 1004) to determine whether to serve relevant advertisements. In certain embodiments, the medical device also obtains geographic position data for a location of the medical device (task 1006).

The medical device automatically determines when a consumable needs to be replenished or replaced (query task 1008) and/or when the patient needs medical treatment or attention (query task 1010). In response to an affirmative determination by query task 1008 or query task 1010, the medical device processes the geographic position data to find relevant advertisers having facilities, stores, offices, or places of business near the current location of the medical device (task 1012). Task 1012 functions to filter the set of stored advertisements such that the medical device can selectively present advertisements associated with local entities. As described previously in this section, the medical device can utilize the geographic position data to prepare and generate directions to advertiser facilities (task 1014).

The medical device can then present at least one advertisement, preferably using its native display element (task 1016). The advertisement could identify: a supplier, vendor, or seller of a consumable associated with the medical device; a supplier, seller, or provider of medical services; and/or a supplier, vendor, seller, or provider of goods or services associated with the treatment, management, or diagnosis of a medical condition. The advertisement might also indicate or recommend a quantity, number of units, volume, or amount of a consumable that might be required. The medical device may also provide directions to a facility associated with the displayed advertisement (task 1018), and take further action in connection with the rendering of the advertisement (task 1020). For example, process 1000 might initiate a transaction for a consumable, goods or services, or a product. Alternatively (or additionally), process 1000 might display an active link that can be used to initiate an electronic transaction, or display an HTML document, such as the web page of an advertiser. Process 1000 may also process user input at the medical device, where such user input filters or modifies transactions or recommendations made by the medical device.

A network-enabled medical device could also support a feature that allows it to log into a service provider's website or online store, access available consumables, related products, accessories, etc. In this regard, if the device has a native web browser application and internet connectivity, it could be used to complete web-based electronic transactions in a manner that is akin to placing an online order from the user's personal computer. In alternate embodiments, the user could use the medical device to initiate orders for consumables, accessories, or products in an "offline" manner. Such orders can be saved and queued by the medical device for subsequent processing at a time when the medical device has network connectivity. For example, some medical devices may be configured to link with a base station device that is located at the patient's home—the base station might be a network-enabled appliance. When the medical device establishes connectivity with the base station device, the queued orders can be processed and completed with the assistance of the base station device.

Device Learning

A medical device as described herein may be suitably configured to perform certain intelligent learning operations that enhance the overall user experience. For example, a medical device could be designed to detect and learn features and functions that are used or accessed most often (and, conversely, those features and functions that are rarely used or accessed), and modify the display menu structure in a way that makes it easier for the user to access and activate the common features. In this regard, common features and functions might be provided on a main/home menu screen or provided on a menu screen that is easy to navigate to. On the other hand, rarely used features and functions may be embedded deeper into the menu structure so that they do not interfere with or otherwise impede the routine operation of the device.

As another example, the device may gradually introduce advanced features and functions to the user only after it has detected a threshold amount of use or experience associated with the user. The device might use a simple timer and unlock, or provide tutorials for, new or advanced features only after the device has been in use for a predetermined amount of time, e.g., a month. Alternatively, the device could monitor actual use or delivery of therapy and introduce different or advanced features only after the device has been used to administer a certain amount of therapy. In this regard, an insulin infusion pump may gradually introduce more features to the user after it detects the activation of 20, 50, and 100 boluses. This type of gradual introduction ensures that the user is ready and experienced enough to learn new features.

A medical device may also be suitably configured to learn patient habits, usage patterns, or trends, and make adjustments or recommendations as appropriate. For example, if the device determines that a diabetic patient tends to experience high glucose levels an hour after each meal, then the device might suggest an extended bolus prior to the next meal. The extended bolus feature might be an advanced feature that remains hidden or locked by the medical device until it determines that the patient might benefit from that feature. Such hidden and intelligently deployable features can be utilized to make the medical device appear simple or complex in a customized manner to suit the needs and experience of the individual patient.

Device learning features may also consider physiological and/or other information associated with the patient. For example, the medical device could consider the age, weight, and sex of the patient and make adjustments or recommendations as appropriate. The medical device could also consider other medications being used by the patient for purposes of customization, recommendations, and the like.

Dual-Use Devices

As mentioned previously, one controller device could be configured to control two or more therapy delivery devices. In an insulin infusion system, for example, a single wireless controller device can control both a standard tube-based insulin pump and a compact patch pump, if so desired. In another embodiment, a single reconfigurable pump component could be designed to function in a manner akin to a standard tube-based insulin pump and, alternatively, as a patch pump. Such a dual-use pump could be realized by modifying a patch pump such that it can accommodate an optional infusion set. Thus, the dual-use pump could use an infusion set so that it can be held or carried by the patient (e.g., clipped onto a belt). In its patch pump mode of operation, the dual-use pump can be affixed directly to the patient's skin without using an infusion set.

An alternate version of a dual-use pump utilizes a patch pump component that is physically configured in a way that allows it to be "docked" with a standard tube-type pump assembly. A controller device for such dual-use pumps can be designed to control the different physical packages and/or the different modes of operation.

Voice Control and Communication

A medical device as described herein may also support a variety of voice control and communication features that enhance the user experience. For example, the device could be outfitted with a microphone that can be used for voice activated commands. Voice commands may be preprogrammed or customized by the user. If desired, the functions linked to voice commands could be encoded or disguised for secrecy and discretion. For example, rather than linking the saying "administer bolus" to a bolus delivery function, the device could allow the user to program any saying, such as "option three," to an action.

A device may also be designed for voice response compatibility with the communication system or entertainment system of a vehicle. Such compatibility would enable a user to control the medical device while driving—the user would simply need to utter a voice command while the vehicle's system is active and linked to the medical device.

Communication of remote voice commands could also be supported. In this regard, a user of a remote controller device for a therapy delivery device could control the therapy delivery device by uttering a voice command into the controller device. Moreover, voice-over-IP could be used to communicate voice commands when a WLAN network has been detected.

Automatic Reporting

A medical device, such as an infusion pump, may be provided with a notification feature that is used for automatic reporting of status information. In one embodiment, the notification feature is implemented with a simple LED indicator on the housing of the device. This status light could be activated in a coded manner to convey status information. For example, a flashing state might indicate that the device is currently active (e.g., delivering therapy). A continuously lit state might represent a warning condition. Of course, a vast number of patterns, colors, combinations, and states could be utilized to convey different conditions, states, status, and information.

Alarms and Alerts

A medical device as described here may also support enhanced alarm and alerting features. For example, the device may include or communicate with directional or focused speakers that can be selectively activated such that audible alarms can be directed to specified locations rather than generally broadcast. For example, sound-focused emitters could be employed such that audible alarms and alerts are narrowly focused and directed to a specific point or location, while reducing the amount of sound that can be heard elsewhere.

A medical device may also implement adaptive or smart alarm algorithms that can be utilized to reduce the occurrence of nuisance alarms. For example, it might be desirable to temporarily increase the glucose level threshold (associated with a high glucose alarm) immediately following the delivery of a meal bolus, because patients tend to have a spike in glucose level after eating a meal.

Customized Skins

A medical device as described here may be suitably configured to allow the user to customize certain decorative or appearance features. For example, the device may support customizable display wallpapers, screen savers, avatars, and themes. As another option, the device could accept decorative and/or protective skins, cases, holders, covers, face plates, adhesive strips, or the like. Although these decorative features do not affect the functionality of the device, they add value by allowing the user to feel comfortable with his or her medical device, and they reflect a modern approach towards product design.

Predictive Charts

A medical device as described here may utilize predictive charting or graphing techniques that intelligently predict or estimate trends in physiological characteristic data based upon historic and/or empirical data. The predictive feature may be associated with a projected region or range of values corresponding to a future time or period of time. Such predictive data can be displayed on the display element of a therapy delivery device and/or its associated controller device. In practice, the predictive indicia could be rendered as a "layer" on an otherwise standard graphical representation of the physiological characteristic data. In certain embodiments, the predictive display feature can be toggled on and off as desired. This option allows the user to remove the predictive information to avoid confusion with actual or historical data.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method of coordinating control commands in a medical device system comprising a medical device that delivers therapy to a patient, and a plurality of wireless controller devices for the medical device, the method comprising:
   detecting user interaction with the medical device;
   after detecting the user interaction, wirelessly broadcasting a disable message from the medical device, the disable message conveying instructions intended to at least partially disable control functions of the plurality of wireless controller devices;
   thereafter, executing a function of the medical device; and
   after execution of the function, wirelessly broadcasting an enable message from the medical device, the enable message conveying instructions intended to override the effect of the disable message.

2. The method of claim 1, further comprising generating, in response to detecting the user interaction, a control command with the medical device, wherein the control command initiates execution of the function.

3. The method of claim 1, wherein the disable message conveys instructions intended to fully disable all control functions of the plurality of wireless controller devices.

4. The method of claim 1, wherein the disable message conveys instructions intended to selectively disable functions of the plurality of wireless controller devices that influence delivery of therapy to the patient.

5. The method of claim 1, wherein the detecting step occurs when the medical device and all of the plurality of wireless devices are in an idle state.

6. The method of claim 1, wherein the medical device system comprises an insulin infusion system, and the medical device comprises a portable insulin infusion pump that is worn or carried by the patient.

7. A method of coordinating control commands in a medical device system comprising a medical device that delivers therapy to a patient, and a plurality of wireless controller devices for the medical device, the method comprising:
   wirelessly receiving a disable message at the plurality of wireless controller devices, wherein the disable message is broadcast from the medical device in preparation of executing a control command at the medical device;
   in response to receiving the disable message, at least partially disabling control functions of the plurality of wireless controller devices, resulting in at least one disabled function;
   thereafter, wirelessly receiving an enable message at the plurality of wireless controller devices; and
   in response to receiving the enable message, enabling the at least one disabled function of the plurality of wireless controller devices.

8. The method of claim 7, wherein the step of at least partially disabling control functions disables all functions of the plurality of wireless controller devices.

9. The method of claim 7, wherein the step of at least partially disabling control functions selectively disables functions of the plurality of wireless controller devices that influence delivery of therapy to the patient.

10. The method of claim 7, wherein the enable message is wirelessly received from the medical device.

11. The method of claim 7, wherein the medical device system comprises an insulin infusion system, and the medical device comprises a portable insulin infusion pump that is worn or carried by the patient.

* * * * *